(12) United States Patent
Holmes et al.

(10) Patent No.: US 8,057,377 B2
(45) Date of Patent: Nov. 15, 2011

(54) APPARATUS AND METHOD FOR SEPARATING A COMPOSITE LIQUID INTO AT LEAST TWO COMPONENTS

(75) Inventors: Brian M. Holmes, Lakewood, CO (US); Johan-Petter Hagström, Hägersten (SE); Charles L. Hake, Arvada, CO (US)

(73) Assignee: CaridianBCT, Inc, Lakewood, CO (US)

( * ) Notice: Subject to any disclaimer, the term of this patent is extended or adjusted under 35 U.S.C. 154(b) by 937 days.

(21) Appl. No.: 12/063,163

(22) PCT Filed: Aug. 14, 2006

(86) PCT No.: PCT/US2006/031732
§ 371 (c)(1),
(2), (4) Date: Feb. 7, 2008

(87) PCT Pub. No.: WO2007/024550
PCT Pub. Date: Mar. 1, 2007

(65) Prior Publication Data
US 2008/0220959 A1    Sep. 11, 2008

Related U.S. Application Data

(60) Provisional application No. 60/710,373, filed on Aug. 22, 2005.

(51) Int. Cl.
*B04B 1/00* (2006.01)
*B04B 7/12* (2006.01)

(52) U.S. Cl. .... 494/45; 210/360.1; 210/361; 210/380.1; 422/72; 422/533; 422/555; 422/559; 494/16; 494/20

(58) Field of Classification Search ............... 210/360.1, 210/361, 380.1; 422/72, 533, 555, 559; 494/16, 494/20, 45
See application file for complete search history.

(56) References Cited

U.S. PATENT DOCUMENTS

| | | |
|---|---|---|
| 3,297,244 A | 1/1967 | Hein |
| 3,326,458 A | 6/1967 | Meryman et al. |
| 3,679,128 A | 7/1972 | Unger et al. |
| 3,708,110 A | 1/1973 | Unger et al. |
| 3,724,747 A | 4/1973 | Unger et al. |

(Continued)

FOREIGN PATENT DOCUMENTS

DE        10355026        7/2005

(Continued)

OTHER PUBLICATIONS

International Search Report: PCT/US06/31732, mailed Feb. 12, 2007.

(Continued)

*Primary Examiner* — David A Reifsnyder
(74) *Attorney, Agent, or Firm* — Edna M O'Connor; John R Merkling; Laura B Arciniega

(57) ABSTRACT

A bag loader for loading and unloading at least one satellite bag into and from the central compartment of a rotor of an apparatus for separating a composite liquid into at least two components comprises an upper part for removably securing an upper portion of at least one satellite bag; a lower part comprising a receptacle; and an intermediate part connecting the upper part to the lower part and exposing an intermediate portion of a satellite bag.

60 Claims, 14 Drawing Sheets

U.S. PATENT DOCUMENTS

| | | |
|---|---|---|
| 3,737,096 A | 6/1973 | Jones et al. |
| 3,858,796 A | 1/1975 | Unger et al. |
| 3,987,961 A | 10/1976 | Sinn et al. |
| 4,389,207 A | 6/1983 | Bacehowski et al. |
| 4,405,079 A | 9/1983 | Schoendorfer |
| 4,421,503 A | 12/1983 | Latham, Jr. et al. |
| 4,482,342 A | 11/1984 | Lueptow et al. |
| 4,720,284 A | 1/1988 | McCarty |
| 4,850,995 A | 7/1989 | Tie et al. |
| 4,990,132 A | 2/1991 | Unger et al. |
| 5,114,396 A | 5/1992 | Unger et al. |
| 5,427,695 A | 6/1995 | Brown |
| 5,626,749 A | 5/1997 | Lambert et al. |
| 5,632,906 A | 5/1997 | Ishida et al. |
| 5,723,050 A | 3/1998 | Unger et al. |
| 5,738,644 A | 4/1998 | Holmes et al. |
| 5,874,208 A | 2/1999 | Unger |
| 5,964,724 A | 10/1999 | Rivera et al. |
| 6,261,217 B1 | 7/2001 | Unger et al. |
| 6,296,602 B1 | 10/2001 | Headley |
| 6,315,706 B1 | 11/2001 | Unger et al. |
| 6,348,031 B1 | 2/2002 | Unger et al. |
| 6,656,105 B2 | 12/2003 | Hogberg et al. |
| 6,740,239 B2 | 5/2004 | Hogberg et al. |
| 7,166,217 B2 | 1/2007 | Holmes et al. |
| 7,279,107 B2 | 10/2007 | Hogberg et al. |
| 2004/0104182 A1 * | 6/2004 | Holmes et al. ............. 210/512.1 |
| 2004/0209755 A1 * | 10/2004 | Moore et al. ............... 210/512.1 |
| 2005/0045567 A1 | 3/2005 | Holmes et al. |
| 2007/0179423 A1 | 8/2007 | Felt et al. |
| 2007/0203444 A1 | 8/2007 | Felt et al. |
| 2007/0209708 A1 | 9/2007 | Hermann et al. |
| 2007/0284320 A1 | 12/2007 | Menhennett et al. |
| 2008/0053203 A1 | 3/2008 | Hogberg et al. |

FOREIGN PATENT DOCUMENTS

| | | |
|---|---|---|
| EP | 0499891 | 8/1992 |
| EP | 0771569 | 5/1997 |
| WO | WO 92/00145 | 1/1992 |
| WO | WO 01/02037 | 1/2001 |
| WO | WO 01/97943 | 12/2001 |
| WO | WO 03/089027 | 10/2003 |
| WO | WO 2004/018021 | 3/2004 |
| WO | WO 2004/091798 | 10/2004 |
| WO | WO 2005/030398 | 4/2005 |
| WO | WO2007/024551 | 3/2007 |
| WO | WO 2007024550 A2 * | 3/2007 |

OTHER PUBLICATIONS

Search Report of EP 06076580.7-2310, mailed Oct. 1, 2007.

* cited by examiner

US 8,057,377 B2

APPARATUS AND METHOD FOR SEPARATING A COMPOSITE LIQUID INTO AT LEAST TWO COMPONENTS

RELATED APPLICATIONS

This application is a continuation of International Application No.: PCT/US2006/31732, filed Aug. 14, 2006 which claims the benefit of U.S. Provisional Application No. 60/710,373, filed Aug. 22, 2005.

FIELD OF THE INVENTION

The present invention concerns an apparatus and a method for separating a volume of composite liquid into at least two components.

BACKGROUND

The apparatus and method of the invention are particularly appropriate for the separation of biological fluids comprising an aqueous component and one or more cellular components. For example, potential uses of the invention include: extracting a plasma component, a first cellular component including platelets and mononuclear cells, and a second cellular component including red blood cells and granulocytes from a volume of whole blood; washing thawed glycerolized red blood cells in order to extract therefrom red blood cells ready for use.

International patent application WO 2004/018021 describes a method and an apparatus for separating a volume of whole blood into either a plasma component and a red blood cell component or a plasma component, a red blood cell component and a platelet component. The apparatus comprises a centrifuge adapted to cooperate with an annular separation bag for whole blood, which is connected to either a plasma component bag and a red blood cell component bag or a plasma component bag, a red blood cell component bag and a platelet component bag. The centrifuge includes a rotor for spinning the separation bag and centrifuging the whole blood contained therein, the rotor having a turntable for supporting the separation bag and a central compartment for containing the component bags connected to the separation bag; and a squeezing system for squeezing the separation bag and causing the transfer of the plasma component from the separation bag into the plasma component bag, of the red blood cell component into the red blood cell component bag and, as the case may be, of the platelet component into the platelet component bag.

SUMMARY OF THE INVENTION

An object of the invention is to design a centrifugation apparatus that can perform an optimized separation process for separating, in a minimum amount of time, a composite fluid, such as whole blood, into at least two high quality components.

According to the invention, an apparatus for separating a composite liquid into at least two components comprises a rotor having a rotation axis, comprising a central compartment for containing at least one satellite bag connected to a separation bag; a removable bag loading means having a longitudinal axis, for loading and unloading the at least one satellite bag into and from the central compartment, comprising an upper part comprising securing means for removably securing an upper portion of at least one satellite bag to the bag loading means; a lower part comprising a receptacle for containing a lower portion of at least one satellite bag; and an intermediate part connecting the upper part to the lower part and exposing an intermediate portion of a satellite bag having an upper portion secured to the upper part of the loading means and a lower portion inserted in the receptacle; and a guiding means for guiding the bag loading means within the central compartment when inserting the bag loading means into and removing the bag loading means from the central compartment, and for positioning the bag loading means in a determined position within the rotor.

Other additional or alternative characteristics of the apparatus and the bag loading means are as follows.

The bag loading means further comprises a support means against which the at least one satellite bag is pressed under centrifugation forces during rotation of the rotor.

The support means is so designed that a satellite bag has a lower portion that is closer to the rotation axis than an upper portion, when the bag loading means is engaged in the central compartment and the upper portion of the satellite bag is secured to the upper part of the bag loading means.

The upper, intermediate, and lower part of the loading means comprises a continuous wall having an inner side facing the longitudinal axis of the bag loading means, wherein the support means includes a portion of the continuous wall.

The portion of the inner side of the continuous wall has a surface that is tilted with respect to the rotation axis, when the bag loading means is engaged in the central compartment.

A distance between the inner side of the portion of the continuous wall and the longitudinal axis of the bag loading means decreases from an upper part of the bag loading means to a lower part of the bag loading means, and the longitudinal axis of the bag loading means is substantially parallel to the rotation axis when the bag loading means is engaged in the central compartment.

The portion of the inner side of the continuous wall is defined by a frustum of cone having an axis parallel to the longitudinal axis of the bag loading means, and the longitudinal axis of the bag loading means is substantially parallel to the rotation axis when the bag loading means is engaged in the central compartment.

The lower part of the loading means comprises a curved wall connected to the continuous wall, and a distance between the curved wall and the longitudinal axis of the bag loading means decreases towards a lowest end of the bag loading means, and the support means includes a portion of the curved wall.

The continuous wall has substantially a gutter-like shape.

The guiding means is so designed as to position the bag loading means in the central compartment so that a satellite bag secured thereto is substantially located on one side of a plane containing the rotation axis.

The longitudinal axis of the bag loading means substantially coincides with the rotation axis when the bag loading means is engaged in the central compartment, and the receptacle has an inner wall closest to the longitudinal axis that is so shaped that a distance between the inner wall to the longitudinal axis is less than a distance from the longitudinal axis to a point of the bag loading means where an upper inlet/outlet of a satellite bag secured to the bag loading means is located.

The securing means are designed to cooperate with a bag holder comprising an elongated body, two peg-like members connected to the elongated body at a distance corresponding to a distance between two holes at the upper part of a satellite bag, and two retaining elements respectively connected at the ends of the peg-like members for preventing a satellite bag engaged on the peg-like members of a bag holder from escaping therefrom.

The upper part of bag loading means comprises a wall and the securing means comprises two locking recesses in the wall in which the ends of the peg-like members of a bag holder can be engaged and removably locked therein by the retaining elements.

The upper part of the bag loading means comprises a wall and the securing means comprises two apertures in the wall, in which the ends of the peg-like members of a bag holder can be engaged and removably locked therein by the retaining elements.

The wall of the upper part of the bag loading means comprises two guides respectively extending from two lateral sides of the wall to the securing means, for guiding the peg-like members of a bag holder when the latter is pushed towards the wall for engaging the securing means.

The upper part of the bag loading means comprises a wall having a recess for lodging the end of at least one tube embedded in the upper part of a satellite bag.

The upper part of the bag loading means comprises a wall having an upper edge inwardly projecting a lip under which loops of tube can be stuck.

The bag loading means further comprises a latching means for removably securing the bag loading means to the rotor in a position in which the bag loading means is partially engaged in the central compartment.

The latching means is designed to secure the bag loading means to the rotor in a bag loading/unloading position in which at least the intermediate and upper part of the loading means protrude above an opening of the central compartment.

The bag loading means has a larger, regular, cross section and the guiding means has a cross section which is at least partially complementary of the larger cross section of the bag loading means.

The bag loading means comprises a cradle having a longitudinal axis that is substantially parallel to the rotation axis, wherein the cradle comprises a gutter-like wall having an inner concave surface facing the longitudinal axis, and wherein the concave surface is inclined with respect to the longitudinal axis so that a satellite bag secured by a upper portion thereof, within the concave surface, to an upper part of the gutter-like wall, has a bottom portion that is closer to the longitudinal axis than an upper portion thereof.

The inner concave surface of the gutter-like wall is generally frusto-conical.

The cradle further comprises a containing wall connected to a lower part of the gutter-like wall so as to form a closed wall surrounding a lower portion of a satellite bag secured to the gutter-like wall.

A distance between the containing wall to the longitudinal axis is less than a distance from the longitudinal axis to a point of the gutter-like wall where an upper inlet/outlet of a satellite bag secured to the bag loading means is located.

The cradle further comprises a bottom wall connected to the gutter-like wall and the containing wall so as to form a receptacle for receiving a lower portion of a satellite bag, wherein the receptacle has a depth that is smaller than the length of the gutter like wall.

The bottom wall comprises a curved portion having a concavity oriented towards the rotation axis.

The guiding means are designed to position the bag loading means within the central compartment so that the longitudinal axis of the bag loading means is substantially parallel to the rotation axis.

The apparatus further comprises at least two pinch valve members for blocking or allowing a flow of fluid in a transfer tube connecting a satellite bag to a separation bag, wherein each pinch valve member comprises a head including pinching jaws in which a portion of tube can be engaged, and the at least two pinch valve members are mounted on the rotor so that the heads thereof protrude at a periphery and above a level of an opening of the central compartment, opposite the upper part of the bag loading means, when the bag loading means is engaged in the central compartment.

The apparatus further comprises guiding elements for guiding a tube engaged in the pinching jaws of a pinch valve member into the central compartment along a determined direction.

The apparatus further comprises guiding elements for guiding a tube engaged in the pinching jaws of a pinch valve member along a path substantially following an inner periphery of the central compartment.

The guiding means comprises a container fitting within the central compartment of the rotor.

The bag loading means has a larger, regular, cross section and the container comprises a wall having an inner cross section which is at least partially complementary of the larger cross section of the bag loading means.

The container comprises an annular flange connected to an upper part thereof.

The apparatus further comprises at least two pinch valve members for blocking or allowing a flow of fluid in a transfer tube connecting a satellite bag to a separation bag, wherein each pinch valve member comprises a head including pinching jaws in which a portion of tube can be engaged, the at least two pinch valve members are mounted on the rotor so that the heads thereof protrude at a periphery and above a level of an opening of the central compartment, and the flange of the container comprises apertures through which the heads of the pinch valve members can extend.

The guiding means further comprises guiding elements partially surrounding the apertures for the heads of the pinch valve members and defining gates for guiding a tube engaged in a pinch valve member into the container in a determined direction.

The guiding means further comprises guiding elements for guiding a tube engaged in a pinch valve member along a path substantially following an inner periphery of the container.

Other features and advantages of the invention will appear from the following description and accompanying drawings, which are to be considered illustrative only.

For the sake of clarity, the invention will be described with respect to two specific uses, namely the separation of whole blood into three components, and the washing of thawed glycerolized red blood cells. It should be understood however that these specific uses are exemplary only.

Figure 1:
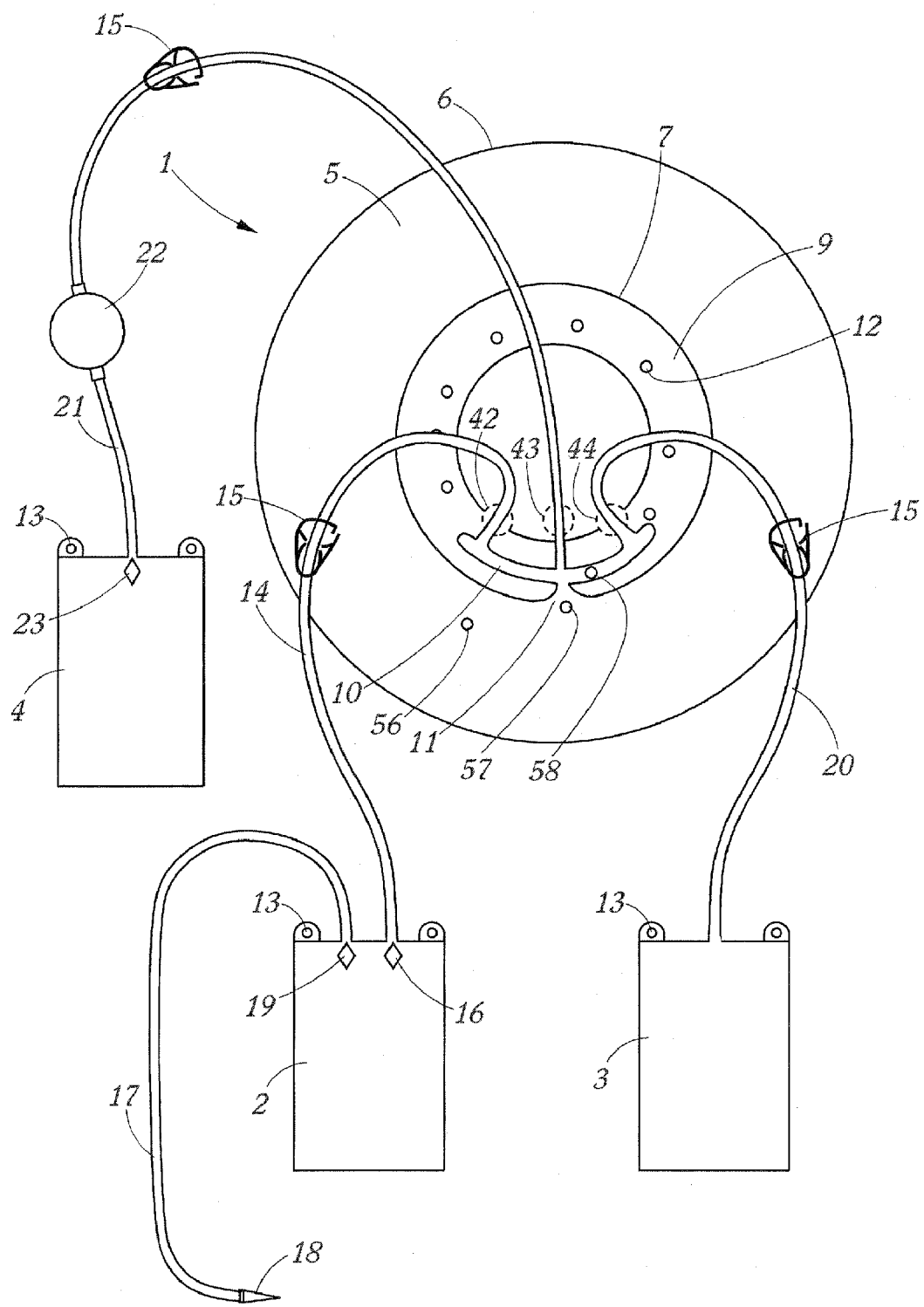
FIG. 1 is a schematic view of first set of separation and collection bags for cooperating with a separation apparatus.

FIG. 1 shows an example of a set of bags adapted to the separation of whole blood into a plasma component essentially comprising plasma, a first blood cell component essentially comprising mononuclear cells and platelets, and a second blood cell component essentially comprising red blood cells. This bag set comprises a flexible separation bag 1 and three flexible satellite bags 2, 3, 4 connected thereto. The separation bag 1 comprises an annular separation chamber 5 having a substantially circular outer edge 6 and an inner circular edge 7. The outer circular edge 6 and the inner circular edge 7 of the separation chamber 5 are substantially concentric. The separation bag 1 further comprises a semi-flexible disk-shaped connecting element 9 that is connected to the inner edge 7 of the annular chamber 5. The disk-shaped connecting element 9 comprises a distribution channel 10 embedded therein, which communicates through a passage 11 with the annular chamber 5. The distribution channel 10 substantially extends along an arc of circle. The disk-shaped connecting element 9 comprises a series of holes 12 for securing the separation bag 1 to the rotor of a centrifuge.

The first satellite bag 2 has two purposes and is successively used as a blood collection bag 2 and as a mononuclear cell/platelet component bag. The first satellite bag is intended for initially receiving a volume of whole blood from a donor (usually about 450 ml) before the separation process, and the mononuclear cell/platelet component during the separation process. The first satellite bag 2 is flat, substantially rectangular, and comprises two reinforced ears at its upper corners having holes 13 for hanging the bag. It is connected to the separation bag 1 by a first transfer tube 14, fitted with a clamp 15. The first transfer tube 14 has a first end connected to the upper edge of the first satellite bag 2 and a second end connected to a first end of the distribution channel 10. The first satellite bag 2 contains a volume of anti-coagulant solution (typically about 63 ml of a solution of citrate phosphate dextrose for a blood donation of about 450 ml). A plug 16 removable from within the first satellite bag 2 (so-called "frangible pin", for example) blocks a liquid flow through the first transfer tube 14 and prevents the anti-coagulant solution from flowing from the first satellite bag 2 into the separation bag 1.

A collection tube 17 is connected at one end to the upper edge of the first satellite bag 2 and comprises, at the other end, a needle protected by a sheath 18. A frangible pin 19 removable from within the first satellite bag 2 plugs the downstream end of the collection tube 17 and prevents the anti-coagulant solution from flowing out of the first satellite bag 2 through the collection tube 17.

The second satellite bag 3 is intended for receiving a plasma component. It is flat, substantially rectangular, and comprises two reinforced ears at its upper corners having holes 13 for hanging the bag. It is connected by a second transfer tube 20 to the separation bag 1. The second transfer tube 20, which is fitted with a clamp 15, has a first end connected to the upper edge of the second satellite bag 3 and a second end connected to a second end of the distribution channel 10.

The third satellite bag 4 is intended for receiving a red blood cell component. It is flat, substantially rectangular, and comprises two reinforced ears at its upper corners having holes 13 for hanging the bag. It is connected by a third transfer tube 21 to the separation bag 1. The third transfer tube 21 has a first end connected to the upper edge of the third satellite bag 4 and a second end that is connected to the distribution channel 10 so as to face the passage 11 between the distribution channel 10 and the separation chamber 5. It comprises two segments respectively connected to the inlet and the outlet of a leuko-reduction filter 22. The tube segment connected to the separation bag 1 is fitted with a clamp 15. The filter 22 may be, for example, a filter of the type RC2D manufactured by Pall Corporation. Such a filter comprises a disk-shaped casing to which radial inlet and outlet ports are connected, in diametral opposition. The third satellite bag 4 contains a volume of storage solution for red blood cells. A plug 23 removable from within the third satellite bag 4 (so-called "frangible pin", for example) blocks a liquid flow through the third transfer tube 21 and prevents the storage solution from flowing from the third satellite bag 4 into the separation bag 1.

Variants of the separation bag 1 may include a separation chamber 5 having an outer circular edge 6 and/or an inner circular edge 7 that are eccentric; a separation chamber 5 that comprises a radial wall extending from the inner edge 7 to the outer edge 6 so that the chamber 5, instead of being annular, is C-shaped; and a separation chamber 5 having any shape including an inner edge and an outer edge (the inner edge being closer to the axis of the rotor of a centrifuge than the outer edge, when the separation bag is mounted on the rotor of a centrifuge), for example of the shape of a portion of annulus delimited by two lateral radial edge or a rectangular shape. In this variant, all the satellite bags may be connected to the inner edge of the separation bag.

Also the separation bag 1 can be shaped so as to fit either on a flat support surface or on a frusto-conical support surface of the rotor of a centrifuge.

Figure 2:
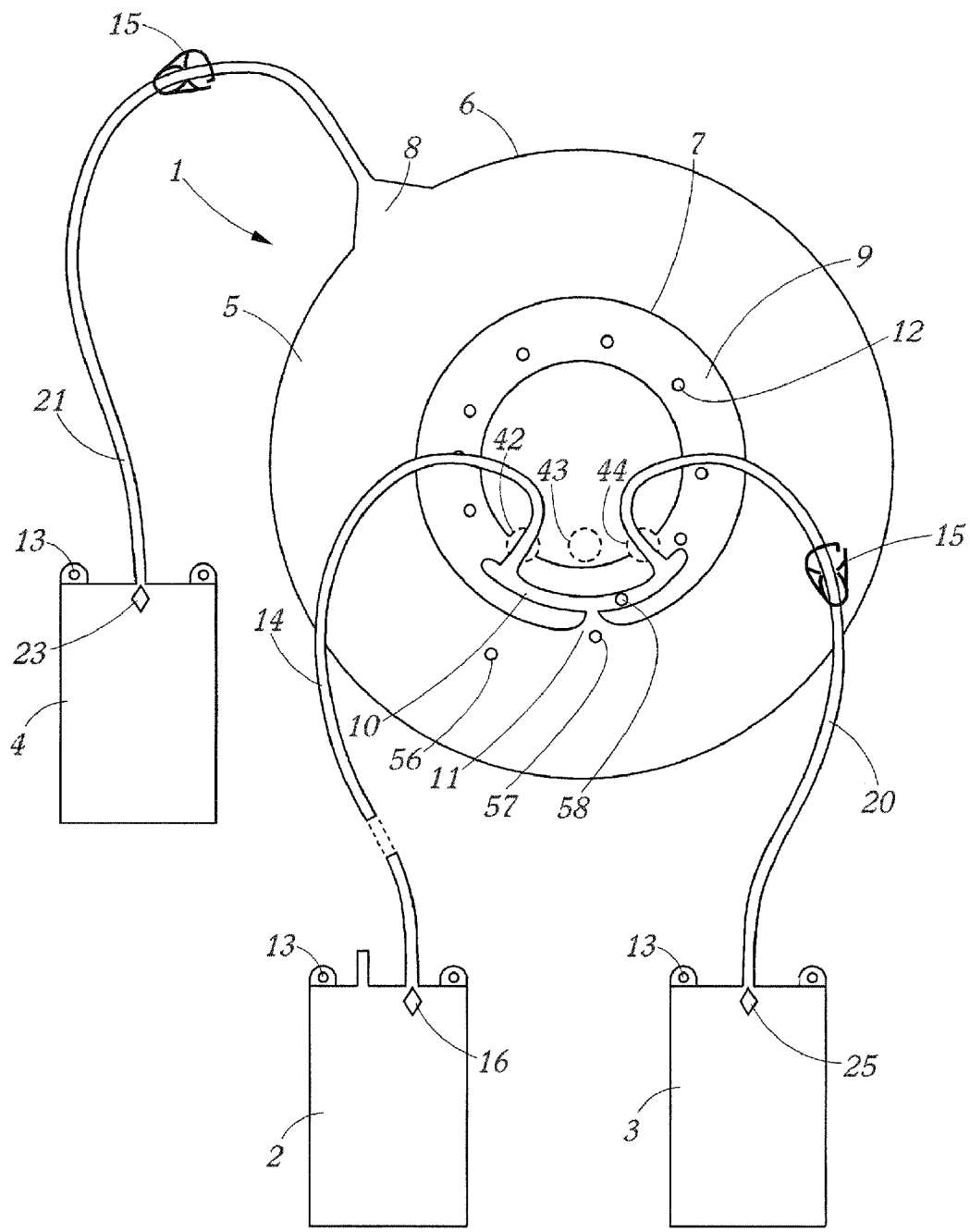
FIG. 2 is a schematic view of second set of separation and collection bags for cooperating with a separation apparatus.

FIG. 2 shows an example of a set of bags adapted to the washing of thawed glycerolized red blood cells. This bag set comprises a separation bag 1 and three satellite bags 2, 3, 4.

The separation bag 1 is identical to the separation bag shown in FIG. 1, save for fact that the separation chamber 5 comprises a funnel like extension 8 protruding outwardly from its outer edge 6 for helping evacuate a content of the separation chamber 5 into the third satellite bag 4.

The first satellite bag 2 contains a volume of thawed glycerolized red blood cells (for example, 300 ml). It is identical to the second satellite bag 2 shown in FIG. 1, except that it is not pre-connected to the separation bag 1. It is connected through a sterile connection process to the first transfer tube 14 just before processing in the centrifuge.

The second satellite bag 3 contains a volume blood washing solution (for example, 700 ml for a volume of glycerolized red blood cells of 300 ml). A plug 25 removable from within (so-called "frangible pin", for example) blocks a liquid flow through the third transfer tube 20 and prevents the blood washing solution from flowing from the second satellite bag 3 into the separation bag 1.

The third satellite bag 4 is intended for receiving washed red blood cells. It is identical to the third satellite bag 4 shown in FIG. 1. The third transfer tube 21 connecting the third satellite bag 4 to the separation bag 1 is not fitted with a leuko-reduction filter.

The bags and the tubes of the first and second bag sets shown in FIGS. 1 and 2 are all made of flexible plastic material appropriate to getting in contact with blood and blood components.

Figure 3:
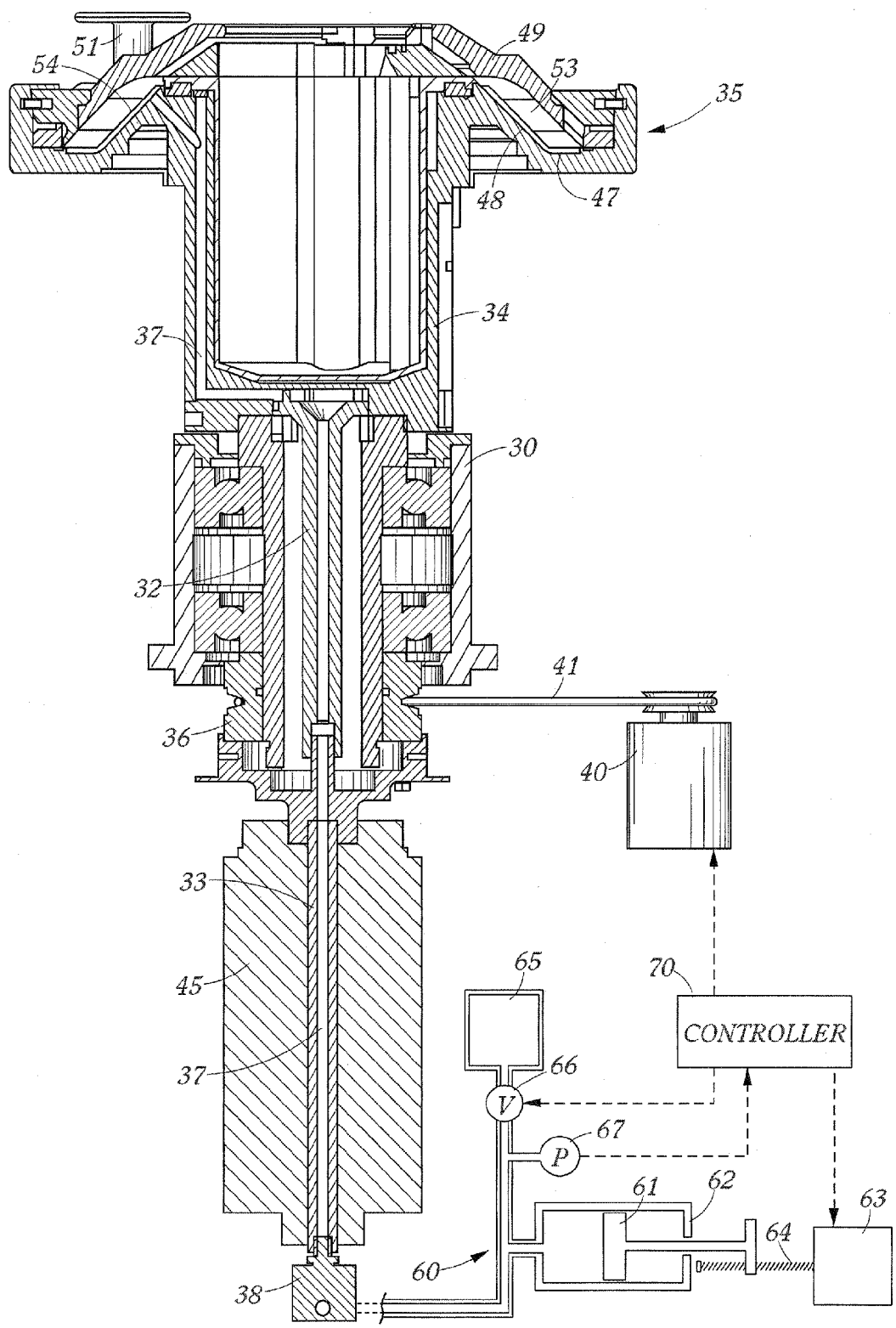
FIG. 3 is a schematic view, partly in cross-section along a diametral plane, of an embodiment of a separation apparatus.
Figure 4:
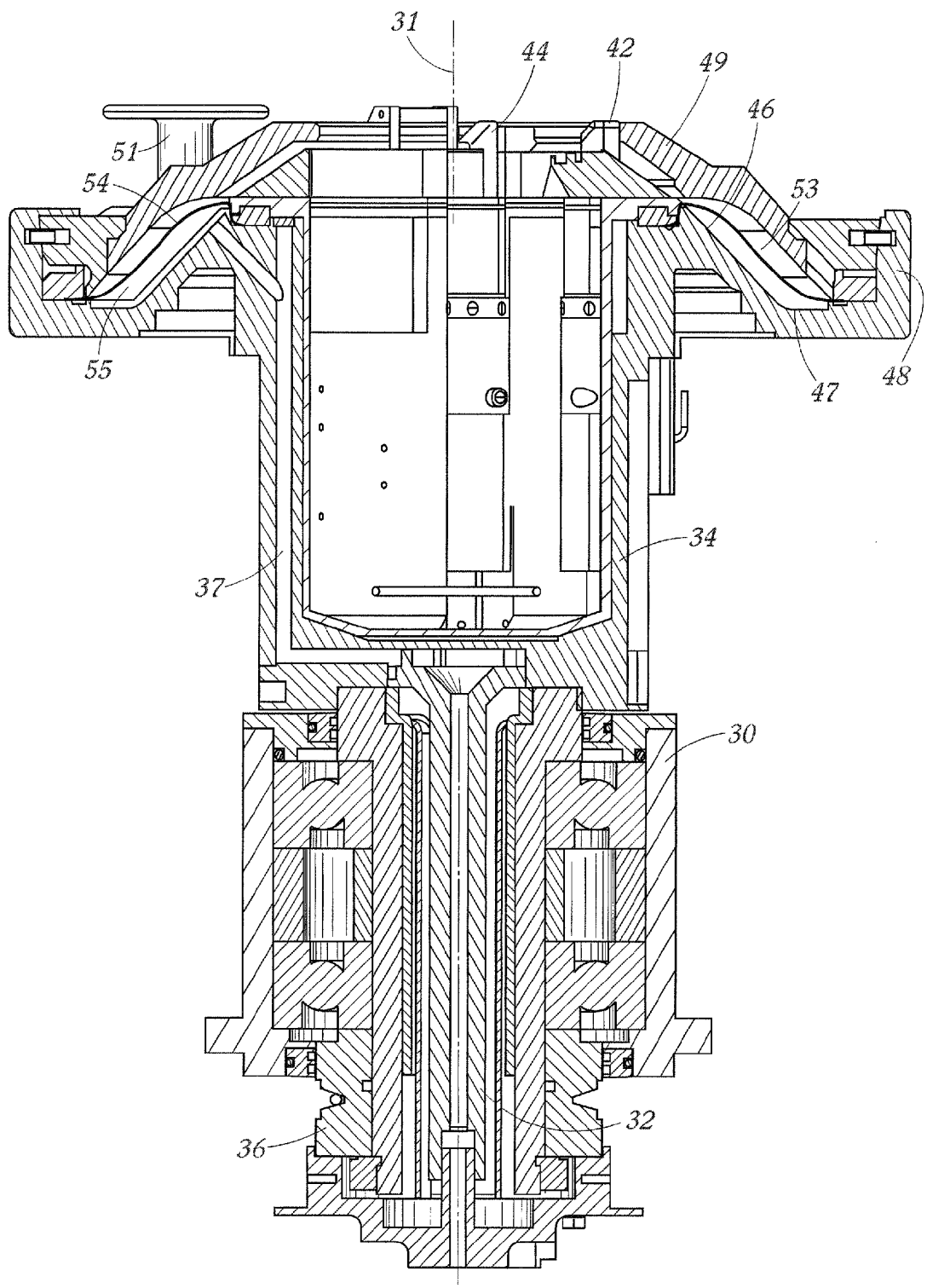
FIG. 4 is a cross-section view, along a diametral plane, of the rotor of the separation apparatus of FIG. 3.

FIGS. 3 and 4 show an embodiment of an apparatus for separating a volume of composite liquid by centrifugation. The apparatus comprises a centrifuge adapted for receiving either set of separation bags shown in FIGS. 1 and 2, and a component transferring means for causing the transfer of separated components into the satellite bags.

The centrifuge comprises a rotor that is supported by a bearing assembly 30 allowing the rotor to rotate about a vertical central axis 31. The rotor comprises a cylindrical rotor shaft 32, 33; a central compartment 34 for containing satellite bags, which is connected to the rotor shaft 32, 33 at the upper end thereof; a support member 87 (not shown in FIGS. 3 and 4) for supporting at least one satellite bag in a determined position within the central compartment 34; and a circular turntable 35 for supporting a separation bag, which is connected to the compartment 34 at the upper end thereof, the central axes of the rotor shaft 31, 32, the compartment 34 and the turntable 35 coinciding with the rotation axis 31.

The rotor shaft comprises a first upper portion 32 and a second lower portion 33.

The upper portion 32 of the shaft extends in part through the bearing assembly 30. A pulley 36 is connected to the lower end of the upper portion 32 of the shaft.

The centrifuge further comprises a motor 40 coupled to the rotor by a belt 41 engaged in a groove of the pulley 36 so as to rotate the rotor about the central vertical axis 31.

The separation apparatus further comprises a first, second and third pinch valve members 42, 43, 44 that are mounted on the rotor for selectively blocking or allowing a flow of liquid through a flexible plastic tube, and selectively sealing and cutting a plastic tube. Each pinch valve member 42, 43, 44 comprises an elongated cylindrical body and a head having a groove that is defined by a stationary upper jaw and a lower jaw movable between an open and a closed position, the groove being dimensioned so that one of the transfer tubes 14, 20, 21 of the bag sets shown in FIGS. 1 and 2 can be snuggly engaged therein when the lower jaw is in the open position. The elongated body contains a mechanism for moving the lower jaw and it is connected to a radio frequency generator that supplies the energy necessary for sealing and cutting a plastic tube. The pinch valve members 42, 43, 44 are mounted at the periphery of the central compartment 34 so that their longitudinal axes are parallel to the central axis 31 of the rotor and their heads protrude above the rim of the compartment 34. The position of the pinch valve members 42, 43, 44 with respect to the separation bag 1 and the transfer tubes 14, 20 connected thereto when the separation bag 1 is mounted on the turntable 35 is shown in doted lines in FIGS. 1 and 2. Electric power is supplied to the pinch valve members 42, 43, 44 through a slip ring array 45 that is mounted around the lower portion 33 of the rotor shaft.

The turntable 35 comprises a central frusto-conical portion 46, the upper, smaller edge of which is connected to the rim of the compartment 34, an annular flat portion 47 connected to the lower, larger edge of the frusto-conical portion 46, and an outer cylindrical flange 48 extending upwards from the outer periphery of the annular portion 47. The turntable 35 further comprises a vaulted circular lid 49 that is secured to the flange 48 by a hinge so as to pivot between an open and a closed position. The lid 49 is fitted with a lock 51 by which it can be blocked in the closed position. The lid 49 comprises a large cut-out in its upper part that gives access to the central compartment 34 of the rotor. The lid 49 has an annular interior surface that is so shaped that, when the lid 49 is in the closed position, it defines with the frusto-conical portion 46 and the annular flat portion 47 of the turntable 38 a frusto-conical annular compartment 53 having a radial cross-section that has substantially the shape of a parallelogram. The frusto-conical annular compartment 53, later the "separation compartment", is intended for containing the separation bag 1 shown in FIGS. 1 and 2.

The component transferring means comprises a squeezing system for squeezing the separation bag within the separation compartment 53 and causing the transfer of separated components into the satellite bags. The squeezing system comprises a flexible annular diaphragm 54 that is so shaped as to line the frusto-conical portion 46 and the annular flat portion 47 of the turntable 35, to which it is secured along its smaller and larger circular edges. The squeezing system further comprises a hydraulic pumping station 60 for pumping a hydraulic liquid in and out an expandable hydraulic chamber 55 defined between the flexible diaphragm 54 and the turntable 35, via a duct 37 extending through the rotor from the lower end of the lower portion 33 of the rotor shaft to the turntable 35. The pumping station 60 comprises a piston pump having a piston 61 movable in a hydraulic cylinder 62 fluidly connected via a rotary fluid coupling 38 to the rotor duct 37. The piston 61 is actuated by a stepper motor 63 that moves a lead screw 64 linked to the piston rod. The hydraulic cylinder 62 is also connected to a hydraulic liquid reservoir 65 having an access controlled by a valve 66 for selectively allowing the introduction or the withdrawal of hydraulic liquid into and from a hydraulic circuit including the hydraulic cylinder 62, the rotor duct 37 and the expandable hydraulic chamber 55. A pressure gauge 67 is connected to the hydraulic circuit for measuring the hydraulic pressure therein.

The separation apparatus further comprises three sensors 56, 57, 58 for detecting characteristics of the separation process occurring within a separation bag when the apparatus operates. The three sensors 56, 57, 58 are embedded in the lid 49 at different distances from the rotation axis of the rotor, a first sensor 56 being the farthest to the rotation axis, a third sensor 58 being the closest to the rotation axis and a second sensor 57 occupying an intermediate position. When the lid 49 is closed, the three sensors 56, 57, 58 face the separation bag 1 as shown in FIGS. 1 and 2. The first sensor 56 (later the "bag sensor") is embedded in the lid 49 so as to be positioned over the separation chamber 5, at about one third of the width of the separation chamber from the inner edge 6 thereof, and it is offset with respect to the passage 11 between the separation chamber 5 and the distribution channel 10. The bag sensor 56 is able to detect the presence or absence of a liquid in the separation chamber 5, as well as red blood cells in a liquid. The second sensor 57 (later the "bay sensor") is embedded in the lid 49 so as to be positioned over the passage 11 between the separation chamber 5 and the distribution channel 10. The bay sensor 57 is in the pathway of any component flowing from the separation chamber 5 into the three satellite bags 2, 3, 4. The bay sensor 57 is able to detect the presence or absence of a liquid in the distribution channel 10 as well as to detect red blood cells in a liquid. The third sensor 58 (later the "channel sensor") is embedded in the lid 49 so as to be positioned over the distribution channel 10. The channel sensor 58 is in the pathway of any component flowing from the separation chamber 5 into the second satellite bag 3. The channel sensor 58 is able to detect the presence or absence of a liquid in the distribution channel 10 as well as to detect red blood cells in a liquid. Each sensor 56, 57, 58 can comprise a photocell including an infra-red LED and a photodetector. Electric power is supplied to the sensors 56, 57, 58 through the slip ring array 45.

The separation apparatus further comprises a controller 70 including a control unit (microprocessor) and a memory for providing the microprocessor with information and programmed instructions relative to various separation protocols and to the operation of the apparatus in accordance with such separation protocols. In particular, the microprocessor is programmed for receiving information relative to the centrifugation speed(s) at which the rotor is to be rotated during the various stages of a separation process, and information relative to the various transfer flow rates at which separated components are to be transferred from the separation bag 1 into the satellite bags 2, 3, 4. The information relative to the various transfer flow rates can be expressed, for example, as hydraulic liquid flow rates in the hydraulic circuit, or as rotation speeds of the stepper motor 63 of the hydraulic pumping station 60. The microprocessor is further programmed for receiving, directly or through the memory, information from the pressure gauge 67 and from the photocells 56, 57, 58 and for controlling the centrifuge motor 40, the stepper motor 63, and the pinch valve members 42, 43, 44 so as to cause the separation apparatus to operate along a selected separation protocol.

The rotor further comprises a rotor liner fitting within the central compartment 34, and a bag loader (or bag cradle) fitting within the rotor liner, for receiving the satellite bags, the transfer tubes and a leuko-reduction filter and for holding the bags in a determined position. FIGS. 5 to 8 show a first embodiment of a rotor liner 79 and a bag cradle 87. One of the functions of the bag cradle 87 is to serve as a bag loading means for loading/unloading at least one satellite bag into/from the central compartment 34 of the rotor. One of the functions of the rotor liner 79 is to serve as a guiding means for guiding the bag cradle 87 within the central compartment 34 when the bag cradle 87 is inserted into and removed from the central compartment 34, and for positioning the bag cradle 87 in a determined position within the rotor.

The rotor liner 79 comprises a container 120 having a bottom wall 80 and a lateral wall 81, and a flange 82 that is connected to the container 120 slightly below the upper rim of the lateral wall 81.

The lateral wall 81 is substantially defined by a frustum of cone flaring upwards, which is intersected by a flat plane extending in parallel to the axis of the frustum of cone. The lateral wall 81 has therefore a first portion that is a sector of a frustum of cone, connected to a second portion that is flat and has the shape of a parallelogram. The axis of the frustum of cone partially defining the first portion of the lateral wall 81 (which forms also a longitudinal axis of the rotor liner 79) coincides with the rotation axis 31 of the rotor. The angle of the frustum of cone is about 3 degrees. It could be more open. However, the larger the angle, the smaller the space available inside the rotor liner 79 for storing satellite bags.

The upper rim of the lateral wall 81 is inwardly bent over about two thirds of its circumference so as to form a narrow circular lip 84 underneath which loops of tube can be stuck. The lip 84 extends in a plane that is substantially perpendicular to a longitudinal axis of the rotor liner 79.

The flange 82 is annular and has the shape of a frustum of cone flaring downwards at an angle of about 85 degrees. A series of rounded pins 83 arranged on a circle protrude upwards from the flange 82. The size and the location of the pins 83 correspond to the size and location of the holes 12 in the semi-flexible disk-shaped connecting element 9 of a separation bag 1. The pins 83 help position the separation bag 1 on the rotor, and prevent the separation bag 1 from moving with respect to the rotor when the rotor is rotating. Along the flat portion of the lateral wall 81 of the rotor liner 79, the flange 82 comprises three aligned cylindrical apertures 85 that encroach in part on the adjacent flat wall. When the rotor liner 79 is fully inserted in the central compartment 34 of a rotor, the three pinch valve members 42, 43, 44 extend through the apertures 85 so that the heads of the pinch valve members protrude above the flange 82. Three guiding elements 126, 128, 129 of somewhat complex geometrical shapes protrude along the inner periphery of the flange 82, partially surround the three apertures 85, and delimit three narrow gates 86 by which tubes engaged in the pinch valve member 42, 43, 44 can be guided into the central compartment 34 along determined directions.

The rotor liner 79 further comprises a support member for supporting at least one satellite bag full of a liquid and holding it in such a way that the content of the satellite bag is fully transferred into a separation bag connected to the satellite bag when the rotor is rotated at a selected speed. The support member is so designed that a satellite bag received therein has a lower portion that is closer to the rotation axis 31 of the rotor that an upper portion thereof to which a transfer tube is connected.

The support member generally comprises a portion of wall that is tilted with respect to the rotation axis 31 of the rotor. A satellite bag secured by an upper portion thereof to an upper part of the tilted wall is pressed against the tilted wall by centrifugation forces during rotation of the rotor so that a lower portion of the satellite bag is closer to the axis of rotation than an upper portion thereof.

In the embodiment represented in FIGS. 5 to 8, the support member comprises a cradle or bag loader 87 for loading and unloading at least one satellite bag 2, 3, 4 into and from the central compartment 34. The bag loader 87, which forms a removable part of the rotor liner 79, generally comprises an upper part comprising securing means for removably securing an upper portion of at least one satellite bag to the bag loading means; a lower part comprising a receptacle for containing a lower portion of at least one satellite bag; and an intermediate part connecting the upper part to the lower part and exposing an intermediate portion of a satellite bag having an upper part secured to the upper part of the loading means and a lower part inserted in the receptacle.

In more details, the cradle 87 has a first outer, gutter-like, wall 88, which extends over the height of the rotor liner 79, and a second inner, gutter-like, wall 89, which extends from the bottom of the cradle over about one third of the eighth of the rotor liner 79. The inner and outer walls 88, 89 are connected along their lateral edges so that the concavity of the inner wall 89 faces the concavity of the outer wall 88. The first outer wall 88 is a sub-sector of the sector of frusto-conical wall that forms the first portion of the lateral wall 81 of the rotor liner 79. The cradle 87 has a longitudinal axis that coincides with the central axis of the frustum of cone that defines the inner surface of the outer wall 88. As mentioned above, the angle of this frustum of cone is about 3 degrees. When the cradle 87 is fully inserted in the central compartment 34 of a rotor, the longitudinal axis of the cradle 87 coincides with the rotation axis 31 of the rotor. The second inner wall 89 is a sector of a cylinder having a longitudinal axis parallel to the longitudinal axis of the cradle 87. The dimensions of the two walls 88, 89 and the distance between them is so selected that the distance between any point of the inner wall 89 to the longitudinal axis of the cradle 87 is less than the distance from the longitudinal axis to the point (recesses 94, 95) of the outer wall 88 where the inlet/outlet of a satellite bag secured to the outer wall 88 is located. This helps ensure that satellite bags attached to a cradle are confined in an area of a rotor where, under centrifugation forces, the whole content of a satellite can be transferred to a separation bag connected thereto. The cradle 87 further comprises a bottom wall having a flat portion 90, perpendicular to its longitudinal axis, which is connected to the lower rim of the second inner wall 89 (sector of cylinder) and a curved ogival portion 91, which raises from the flat portion 90 to a point located on a median longitudinal axis of the first outer wall 88 (sector of frustum of cone), at about one fifth of the height of the cradle 87, from the flat bottom portion 90. In geometrical terms, the second portion 91 of the bottom of the cradle 87 results from the intersection of a frustum of cone and of a cylinder having perpendicular axes. The second inner wall 89, the lower portion of first outer wall 88 that is connected to the second inner wall 89, and the bottom wall 90, 91 connected thereto, form a receptacle 96 for a lower portion of satellite bags attached to the cradle 87. This receptacle facilitates the insertion of the cradle 87 within the central compartment 34 of a rotor by preventing the lower portion of the satellite bags from interacting with the inner surface of the rotor liner 79.

The cradle 87 further comprises securing means in its upper part, including two lateral recesses 92 opening on its inner surface, for removably receiving and locking the ends of complementary locking elements of a bag holder 100 to be described later. A guide 93, in the form of a narrow tongue, extends from the bottom of each recess 92 towards the lateral edges of the cradle 87 for helping set the bag holder 100 in place. Between the two locking recesses 92, the cradle 87 comprises two other recesses 94, 95 for accommodating the end of transfer tubes embedded in an upper portion of a satellites bag.

Figure 8:
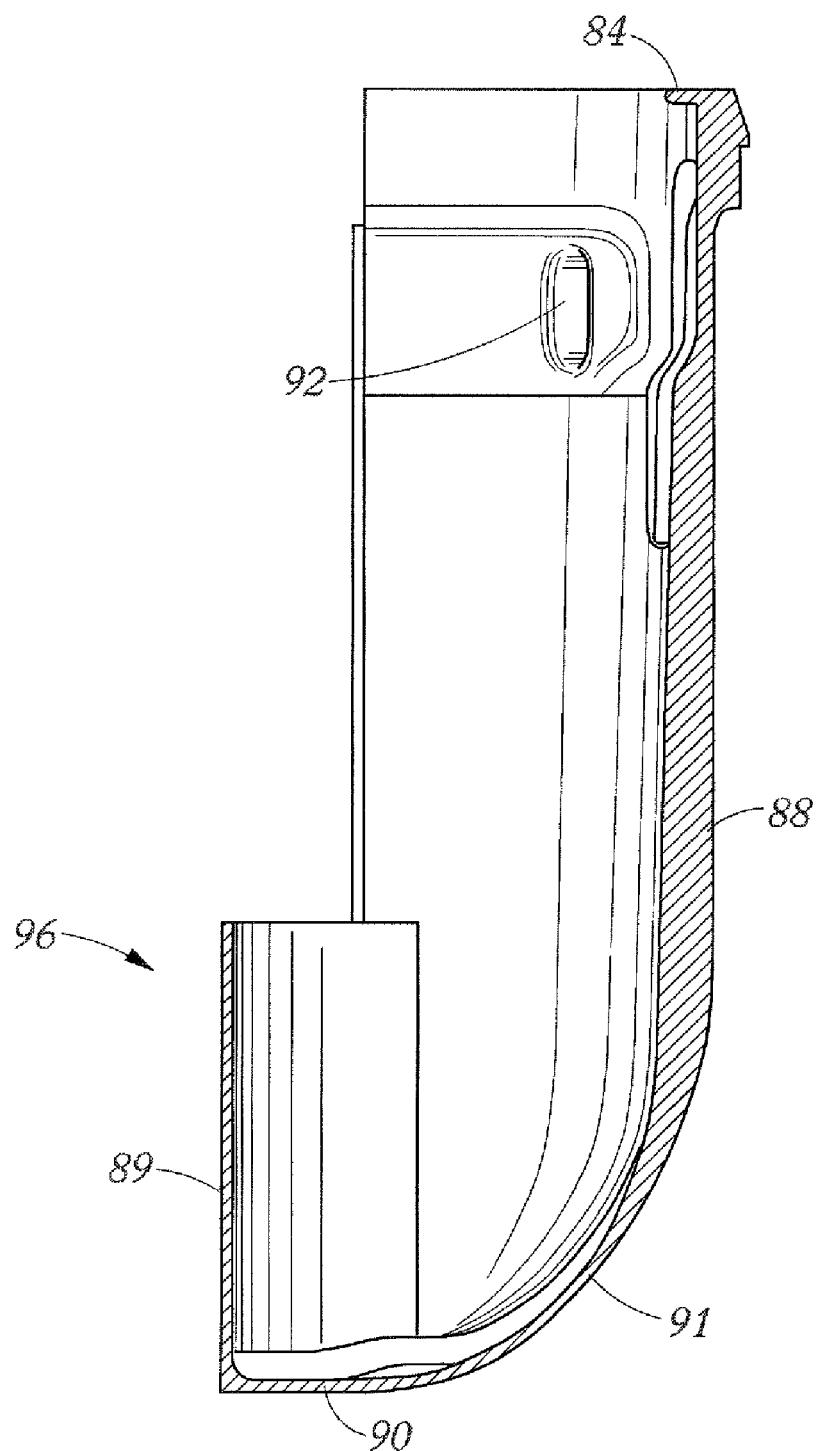
FIG. 8 is a cross section view of a variant of the bag cradle of FIG. 7, along a vertical plane.

As shown in FIG. 8, a variant of the cradle 87 comprises a first outer lateral wall 88 having an uneven thickness, the outer side of the wall 88 being cylindrical, and the inner side of the wall 88 being frusto-conical. This is the inner surface that provides the tilted support for a bag allowing for the outward transfer of its content under centrifugation forces.

As a removable part of the rotor liner 79, the cradle 87 performs a second function, besides enabling the transfer, under centrifugation forces, of the content of a bag secured thereto to the periphery of a rotor. As mentioned above, this second function is a loading function, which, in particular, makes it possible for an operator having two cradles at his disposal to install a second set of bags in a second cradle when a first cradle supporting a first set of bags is spun in a centrifuge, and to load the second cradle in the centrifuge as soon as the first cradle has been removed therefrom after the content of the first set of bags has been processed. This is with respect to this second function that the inner wall 89 of the cradle 87 is helpful. First, because the inner wall 89 is substantially smaller than the opposite outer wall 88, it allows for an easy insertion and arrangement of the lower portion of satellite bags into the bottom area of the cradle 87 (receptacle 96); it also allows for an easy, lateral arrangement of the satellite bags, transfer tubes and, as the case may be, leuko-reduction filter, within the cradle 87; and it allows for an easy, lateral engagement of the pegs 108, 109 of a bag holder 100 into the recesses 92 in the upper part of the outer wall 88 (all these manipulations would be more difficult, had the second inner wall 89 the same height as the first outer wall 88). Second, when a set of satellite bags is secured to the cradle 87 by the bag holder 100, the lower part of the bags are contained in the receptacle 96 defined by the outer wall 88, the inner wall 89, and the bottom wall 90, 91 of the cradle 87 so that the loading of the satellite bags into the rotor liner 89 is straight and can not be impeded by the satellite bags rubbing on the inner surface of the rotor liner 87.

Figure 9:
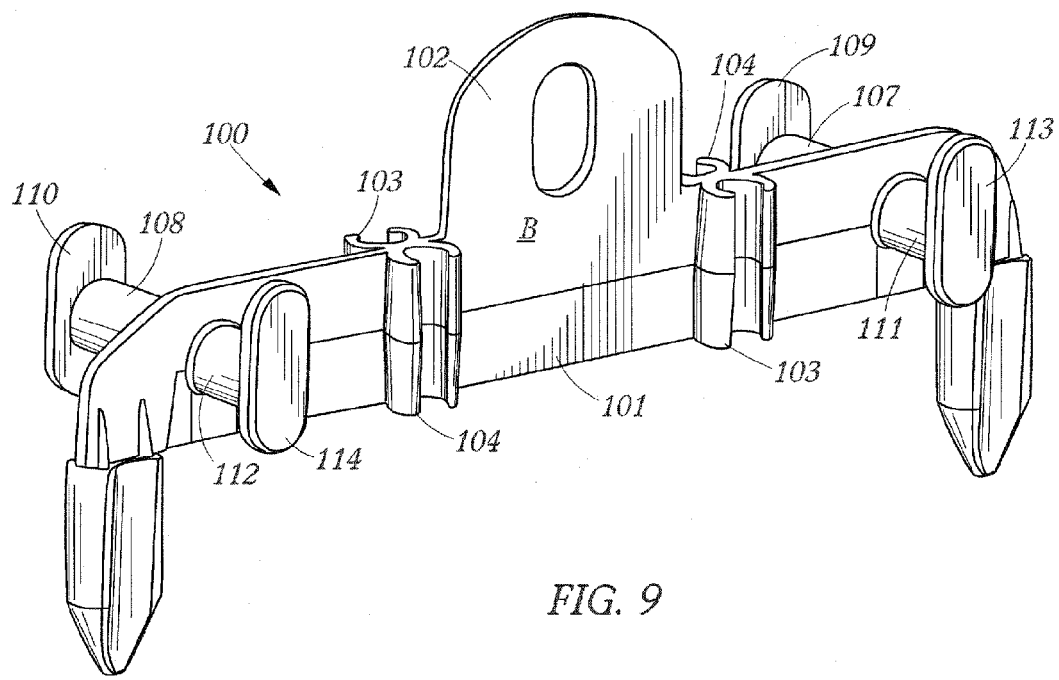
FIG. 9 is a perspective view of a bag holder fitting in the bag cradle of FIGS. 6 to 8.
Figure 10:
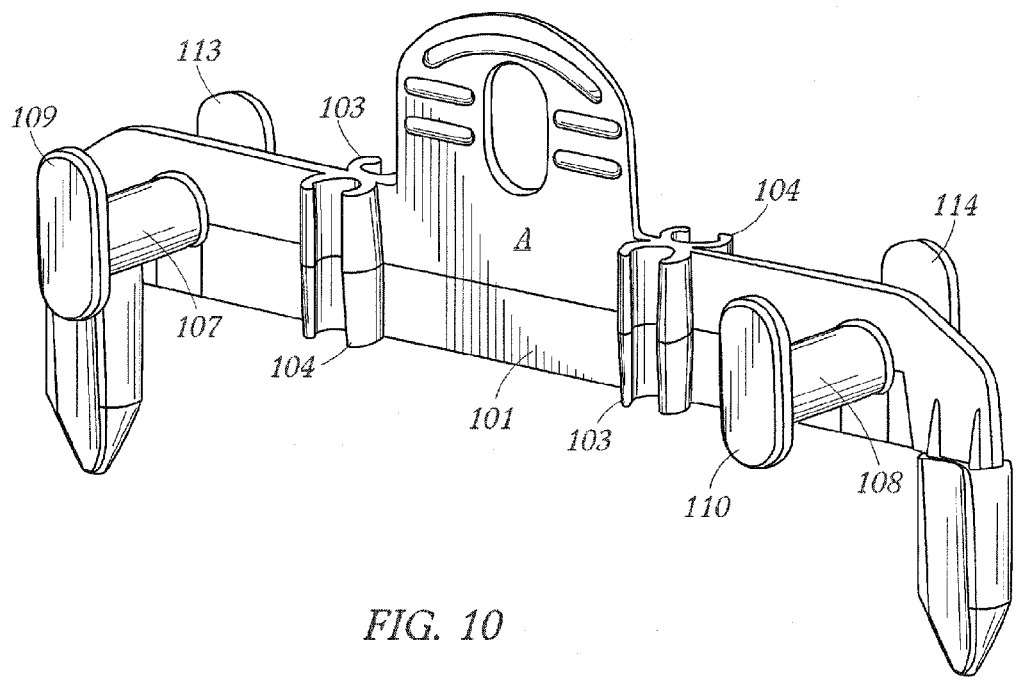
FIG. 10 is a perspective view of a bag holder fitting in the bag cradle of FIGS. 6 to 8.
Figure 11:
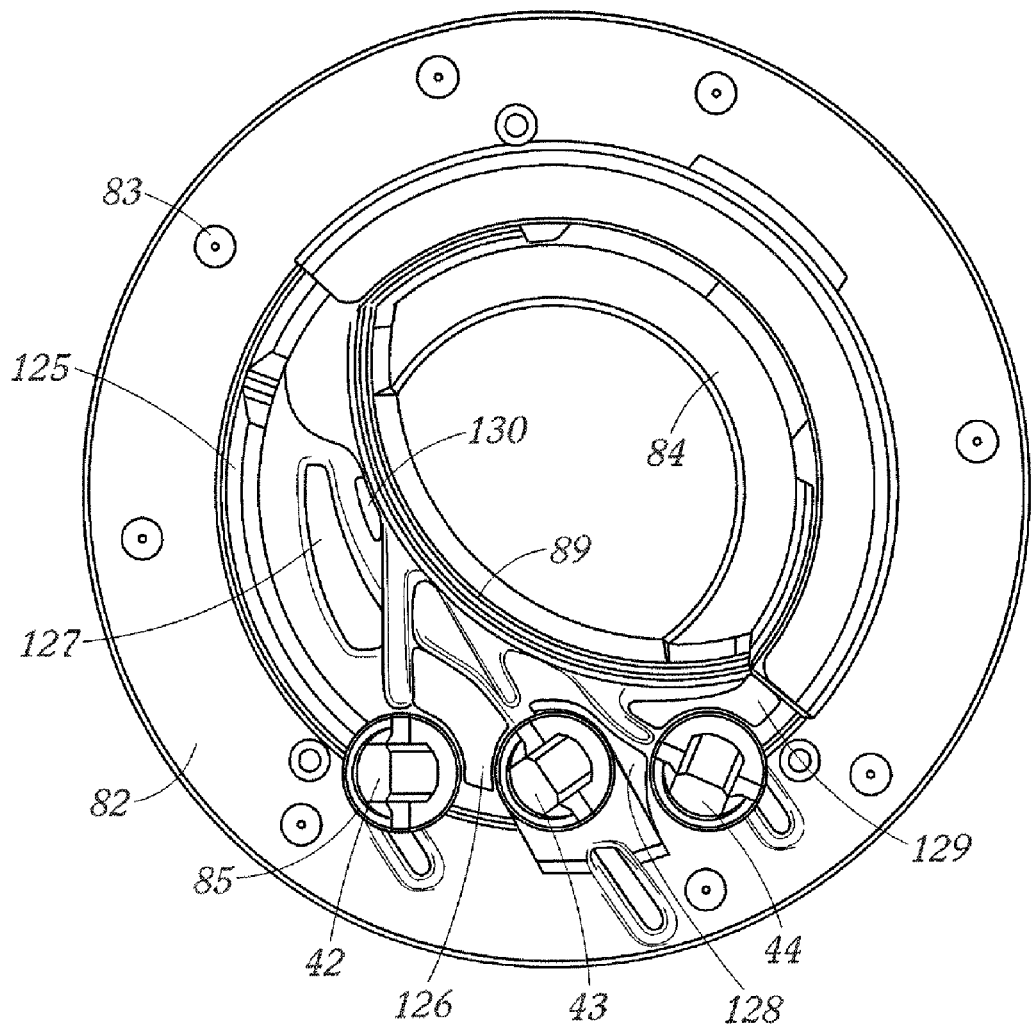
FIG. 11 is a top view of a rotor fitted with a second embodiment of a rotor liner and bag cradle assembly.
Figure 12:
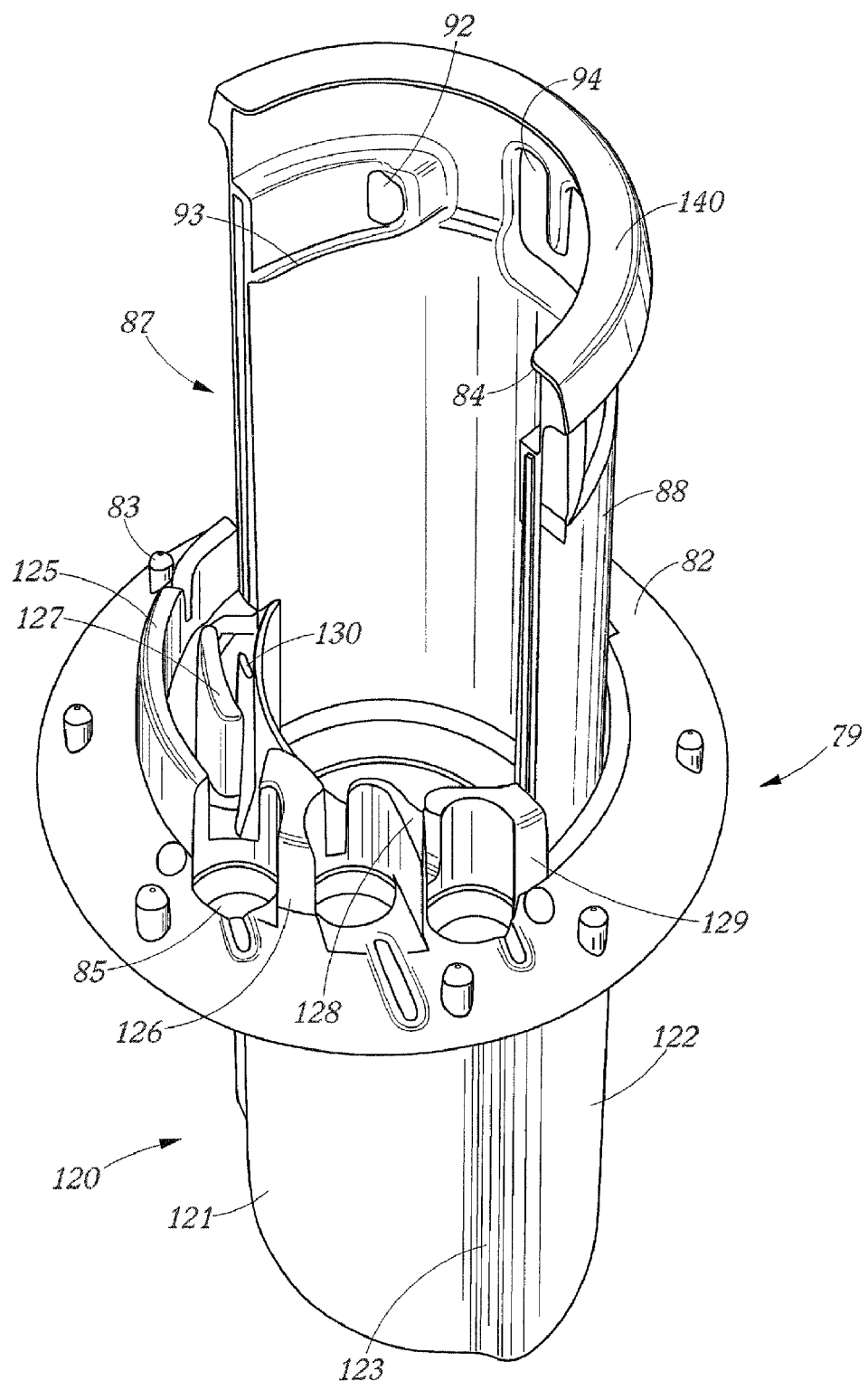
FIG. 12 is a perspective view of the rotor liner and bag cradle assembly of FIG. 11, in which a bag cradle is shown partially withdrawn.
Figure 13:
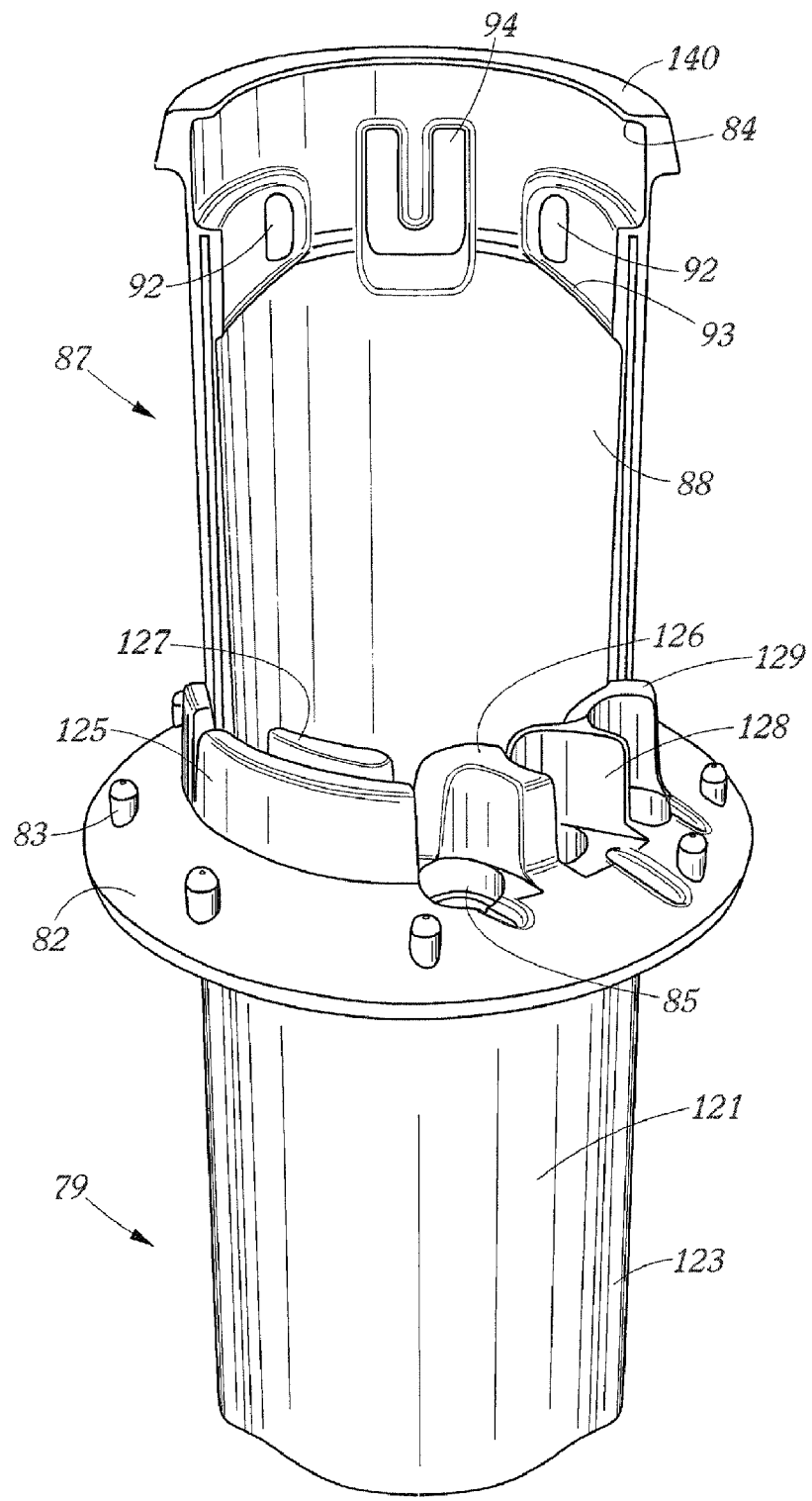
FIG. 13 is a perspective view of the rotor liner and bag cradle assembly of FIG. 11, in which a bag cradle is shown partially withdrawn.
Figure 14:
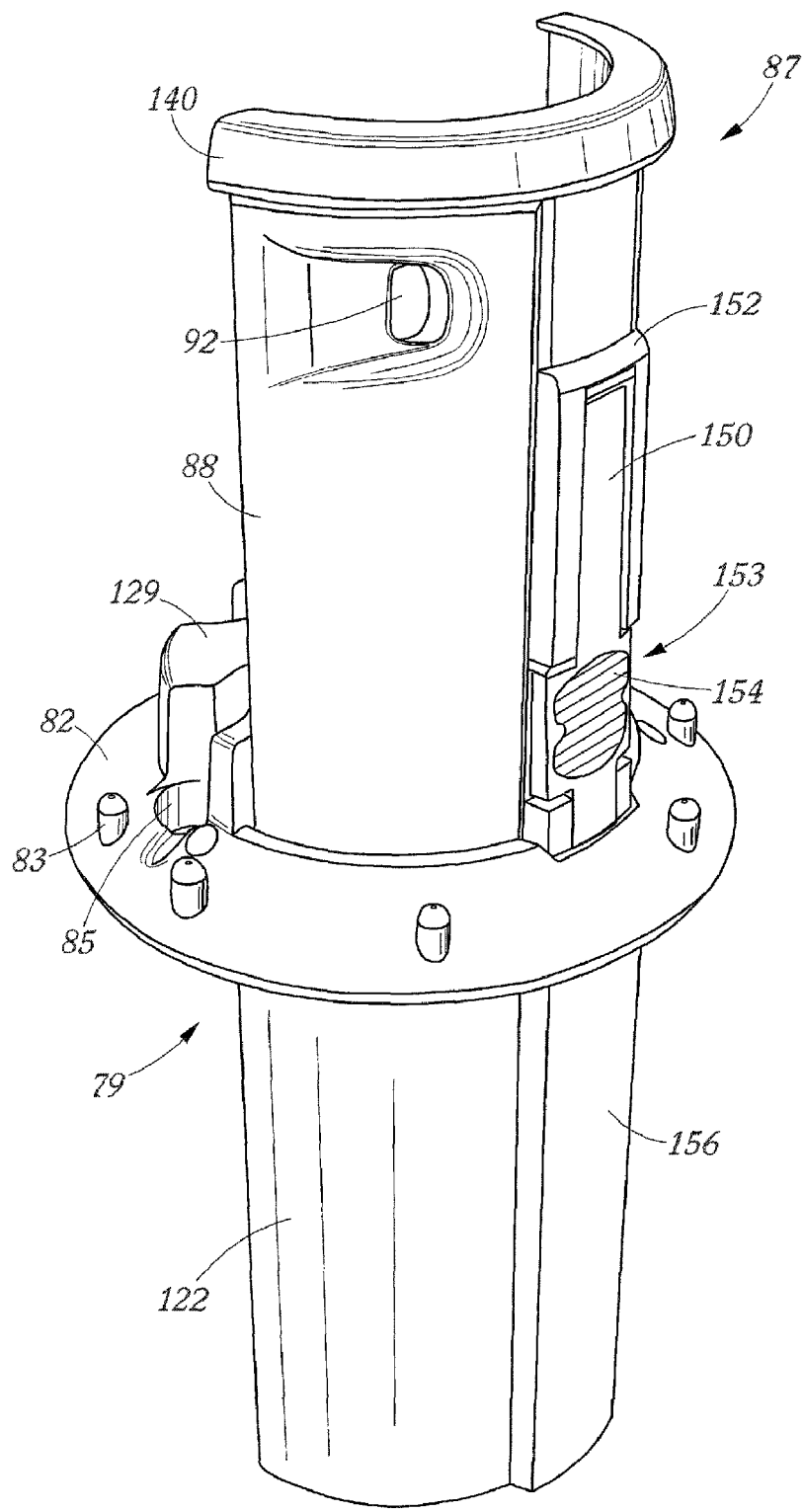
FIG. 14 is a perspective view of the rotor liner and bag cradle assembly of FIG. 11, in which a bag cradle is shown partially withdrawn.
Figure 15:
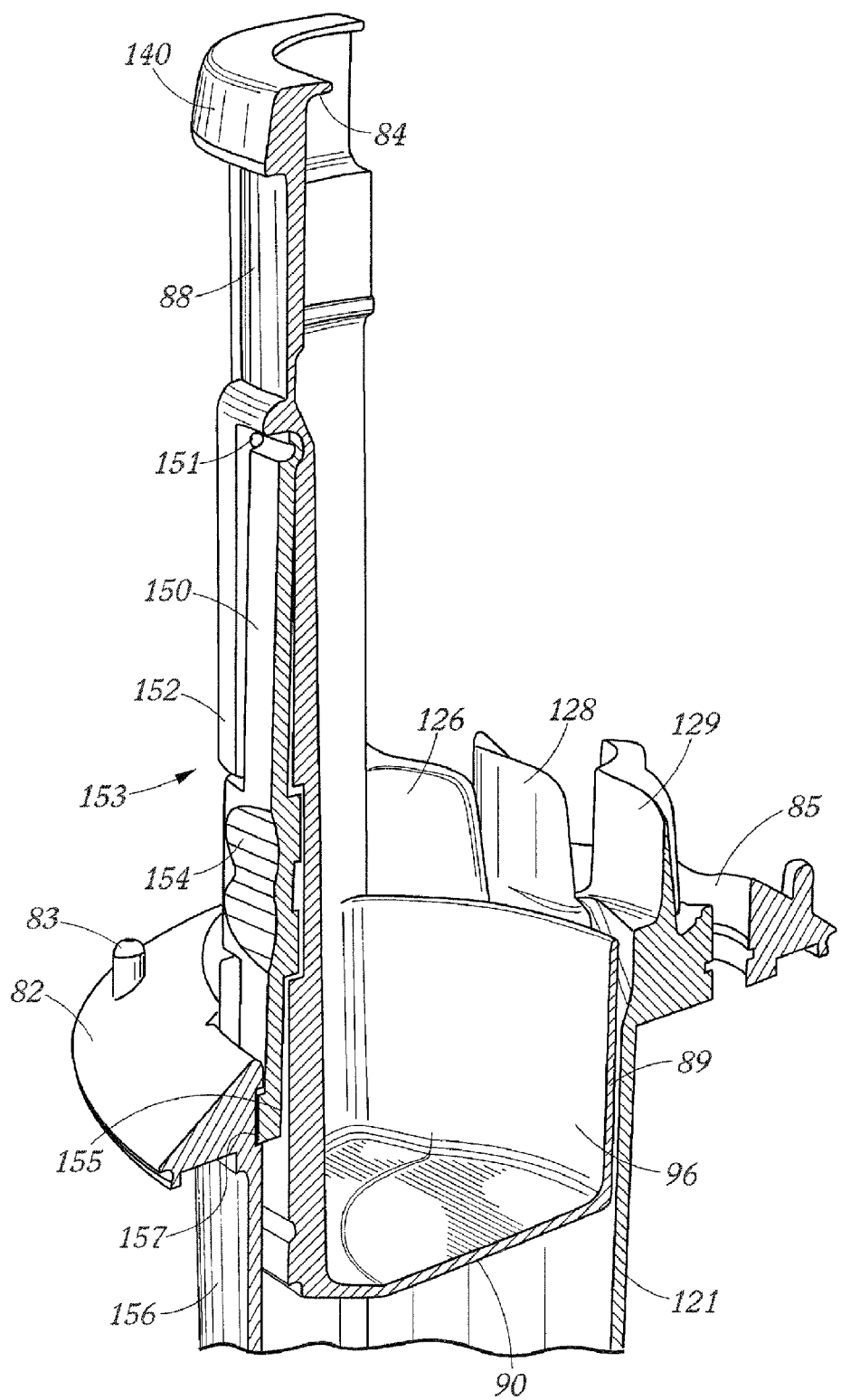
FIG. 15 is a cross section of a perspective view of a detail of the upper part of the rotor liner and bag cradle assembly of FIG. 11.

The bag holder 100 shown in FIGS. 9 and 10 has two main functions. First, it is used during the manufacture and shipping of the bag sets represented in FIGS. 1 and 2 to help assemble the bags together and keep them in a fixed position with respect to each other during sterilization and shipping so that the transfer tubes form large loops and do not kink. Second, the bag holder 100 is used for securing the satellite bags 2, 3, 4 to the cradle 87 in a determined position during the operation of the centrifuge.

The bag-holder 100 comprises an elongated flat body 101 in the middle of which a flat U-shaped handling appendage 102 is connected so as to protrude upwards when the bag-holder 100 is mounted in the cradle 87. The elongated flat body 101 is fitted on both sides A and B with two parallel gutter-like guides 103, 104 that are perpendicular to a longitudinal axis of the elongated flat body 101 and extend in a central portion of the elongated flat body 101, substantially in alignment with the lateral edges of the U-shaped handling appendage 102, respectively. When the bag holder 100 is secured to the cradle 87, the elongated flat body 101 is substantially perpendicular and the gutter-like guides 103, 104 are substantially parallel to the rotation axis 31 of the rotor. The gutter-like guides 103, 104 are so dimensioned that a portion of transfer tube 14, 20, 21 or a needle sheath 18 can be snuggly engaged therein.

The bag-holder 100 further comprises a hanging means in the form of a first couple of pegs 107, 108 connected to the elongated flat body 101 for hanging at least one satellite bag 2, 3, 4 in the cradle 87. The pegs 107, 108 extend perpendicularly from the side A of the elongated flat body 101. The distance between the two pegs 107, 108 is substantially the same as the distance between the holes 13 in the ears of the satellite bags 2, 3, 4. The cross-section of the pegs 107, 108 substantially fits in the holes 13.

The pegs 107, 108 are also used to secure the bag holder 100 to the cradle 87. To this end, the distance between the two pegs 107, 108 is substantially the same as the distance between the two locking recesses 92, 93 in the upper part of the cradle 87. Also, the tip of each peg 107, 108 is fitted with a locking element 109, 110 that can removably lock within a locking recess 92, 93 of the cradle 87. Each locking element 109, 110 is comprised of a plate having rounded ends, which is perpendicularly connected to the corresponding pegs 107, 108.

The bag-holder 100 further comprises a second couple of pegs 111, 112 connected to the elongated flat body 101 for releasably securing a separation bag 1 and, as the case may be, a satellite bag 2, 3, 4 thereto. The pegs 111, 112 extend perpendicularly from the side B of the elongated flat body 101 along the same axis as the pegs 107, 108. The tips of the pegs 111, 112 are fitted with retaining elements 113, 144 for preventing a satellite bag engaged on the pegs from escaping therefrom during centrifugation of the bag assembly. Overall, the second couple of pegs 111, 112 is identical to the first couple of pegs 107, 108 save for the length of the pegs, which is longer in the first couple than in the second couple.

It results from the respective arrangement of the elongated flat body 101 and the first and second couple of pegs 106, 107, 111, 112 that product bags 2, 3, 4 engaged on the pegs occupy a determined position in the central compartment 34 of a rotor when the cradle 87 is assembled to the remaining part of the rotor liner 79. Moreover, when the rotor starts rotating, a satellite bag full of liquid mounted in the cradle 87 by means of the first couple of pegs 106, 107 is stuck by centrifugation forces onto the frusto-conical wall 88 and the rounded bottom part 91 of the cradle 87 so that the upper part of the bag is farther apart from the rotation axis 31 of the rotor than the lower part of the bag. Thanks to this disposition, when the transfer tube connecting the satellite bag to the separation bag is open and the rotation speed is high enough, the liquid initially contained in the satellite bag wholly drains into the separation bag.

Figure 5:
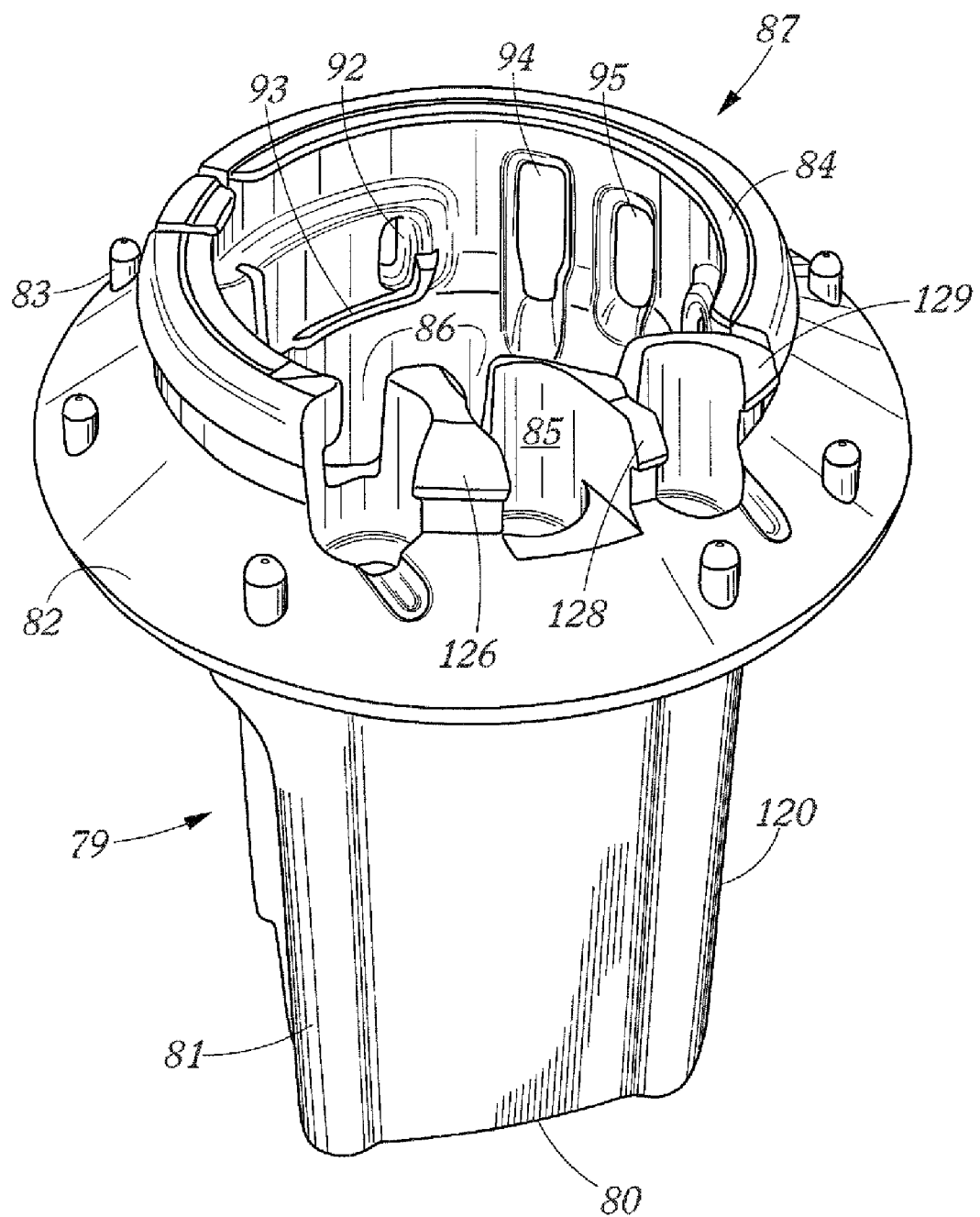
FIG. 5 is a perspective view of a first embodiment of a rotor liner and bag cradle assembly fitting within the rotor of FIG. 4.
Figure 6:
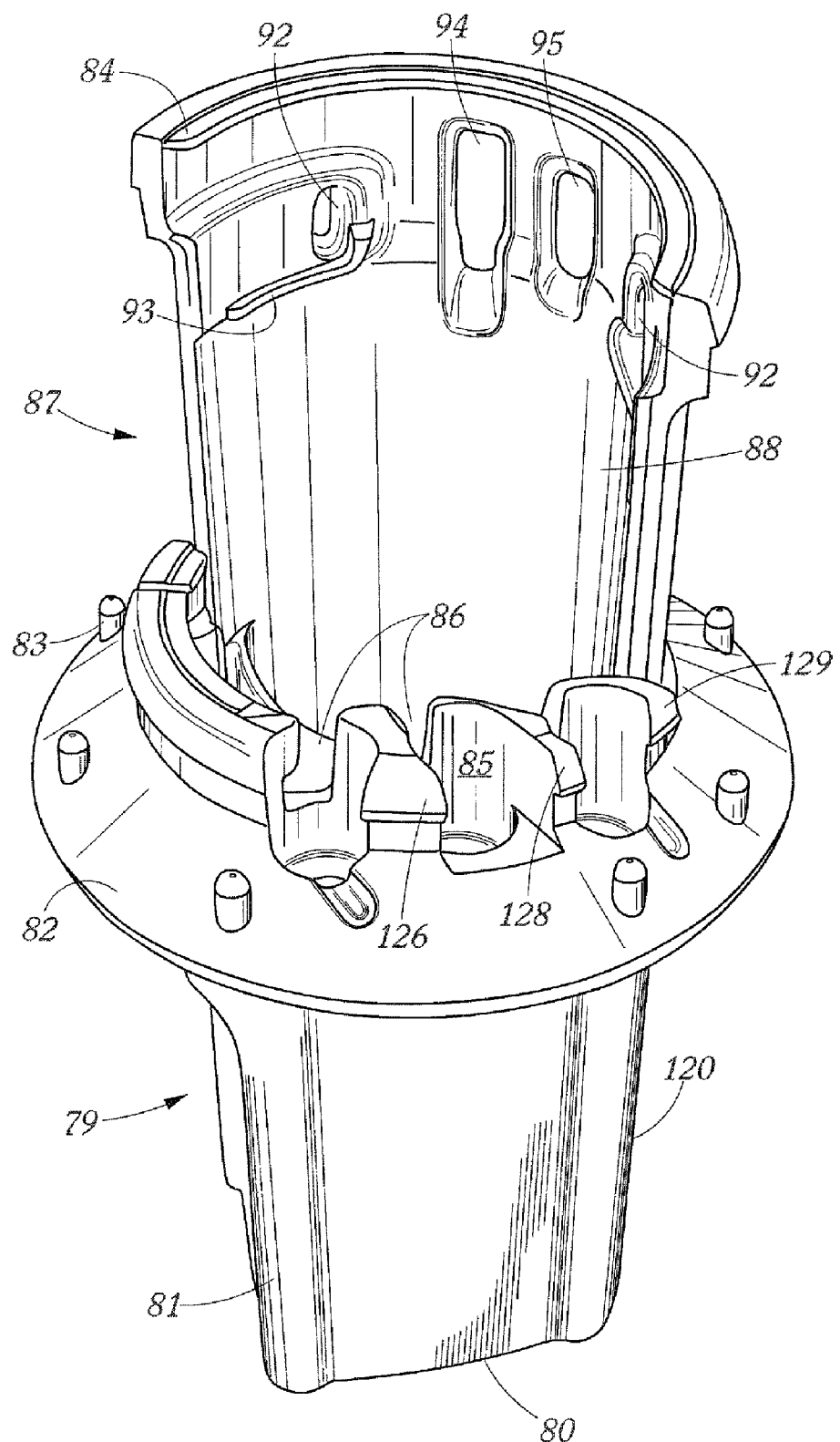
FIG. 6 is a perspective view of the rotor liner and bag cradle assembly of FIG. 4, in which a bag cradle is shown partially withdrawn.
Figure 7:
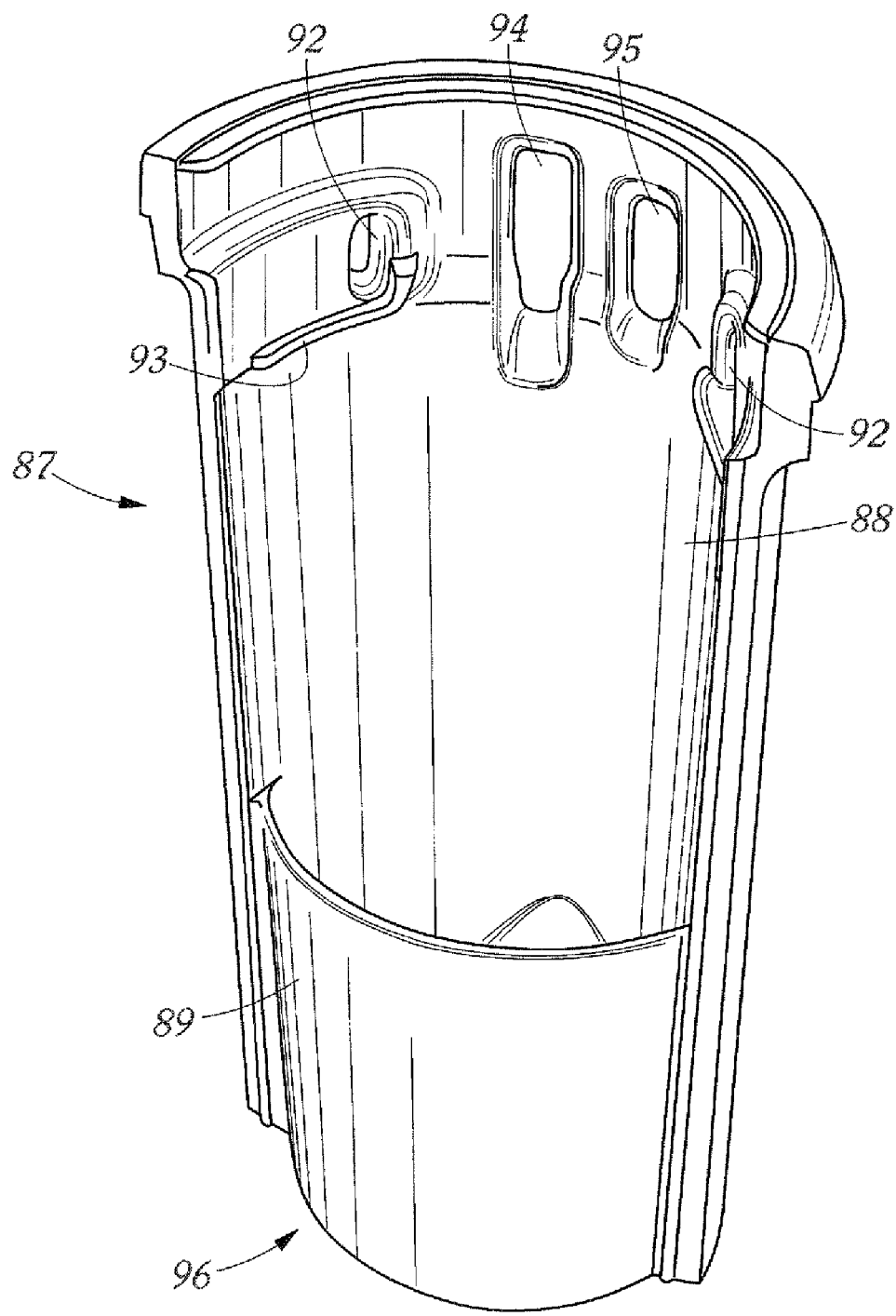
FIG. 7 is a perspective view of the bag cradle of FIG. 6.

FIGS. 11 to 15 show a second embodiment of a rotor liner 79 and bag cradle 87, which, although fulfilling substantially the same functions as the first embodiment shown in FIGS. 5 to 7, comprises structural variants and additional features.

The rotor liner 79 comprises a container 120 including two sections of cylindrical walls 121, 122 that do not have the same curvature. The rotor liner has a longitudinal axis to which the central axes of the two sections of cylindrical walls 121, 122 are parallel. Two elongated walls 123 connect the sections of the cylindrical walls 121, 122 by their lateral edges. In other words, the container 120 has a composite cross section comprising a first arc of circle of larger diameter and a second arc of circle of smaller diameter, the two arcs of circle having their concavities facing each other and being connected together at both ends by two substantially straight lines. The walls of the container 120 are substantially parallel to the axis of rotation 31 of the rotor, when the rotor liner 79 is engaged in the central compartment 34 of the rotor.

The rotor liner 79 comprises a frusto-conical flange 82 that is connected to the upper rim of the container 120 so that the flange 82 flares downwards. The section of the flange 82 that is adjacent the curved wall 121 of smaller curvature comprises three cylindrical apertures 85 whose central axes are coplanar and parallel to the longitudinal axis of the container 120. When the rotor liner 79 is fully inserted in the central compartment 34, the three pinch valve members 42, 43, 44 extend through the three apertures 85 and protrude above the flange 82 so as to expose their respective grooves and allow an easy insertion of a transfer tube 14, 15, 20 therein.

The rotor liner 79 further comprises six guiding elements 125 to 130 of somewhat complex geometrical shape protruding along the inner periphery of the section of the flange 82 that is adjacent to the curved wall 121 of smaller curvature. The main purpose of the guiding elements 125 to 130, which partially surround the three apertures 85 (i.e. the pinch valve members 42, 43, 44), is to orient the transfer tubes 14, 20, 21 within the central compartment 34 so that they form large bends generally following the inner surface of the container 120 between the pinch valves member 42, 43, 44 and the top of the satellite bags attached to the upper part of the cradle 87. It results from this arrangement that the transfer tubes and their content are subjected to substantially even centrifugation forces when the rotor rotates, which facilitates an optimal flow of liquid through the transfer tubes during rotation of the rotor.

A first guiding element 125 comprises a curved guiding wall that extends along a portion of the periphery of the container 120, above the flange 82, between the aperture 85 for the first pinch valve member 42 and a first end of the curved wall 121 of smaller curvature. In other words, one end of the guiding wall 125 abuts a bag cradle 87 engaged in the rotor liner 79 and the other end is adjacent to the inner surface of the cylindrical aperture 125 through which the first pinch valve member 42 extends.

A second guiding element 126 partially surrounds the aperture 85 for the first pinch valve member 42 and the aperture 85 for the second pinch valve member 43. The first and second guiding elements 125, 126 define between them a slot parallel to the longitudinal axis of the rotor liner 79, through which a transfer tube 14 engaged in the first pinch valve member 42 can extend and is directed towards the inner surface of the rotor liner 79.

A third guiding element 127 comprises a guiding wall that extends in parallel to a portion of the guiding wall 125, inside the rotor liner 79. The first and third guiding elements 125, 127 define between each other a groove in which a transfer tube 14 engaged in the first pinch valve member 42 can be inserted so as to follow the inner surface of the rotor liner 79.

A fourth guiding element 128 partially surrounds the aperture 85 for the second pinch valve member 43 and the aperture 85 for the third pinch valve member 44. The second and fourth guiding elements 126, 128 define between them a slot parallel to the longitudinal axis of the rotor liner 79, through which a transfer tube 21 engaged in the second pinch valve member 43 can extend and is directed towards the inner surface of the rotor liner 79.

A fifth guiding element 129 partially surrounds the aperture 85 for the third pinch valve member 44 and extends to a second end of the curved wall 121 of smaller curvature of the container 120. The fourth and fifth guiding elements 128, 129 define between them a slot parallel to the longitudinal axis of the rotor liner 79, through which a transfer tube 20 engaged in the third pinch valve member 44 can extend and is directed towards the inner surface of the rotor liner 79.

A sixth guiding element 130 comprises a guiding wall that extends in parallel to a portion of the third guiding element (guiding wall 127), closer to the inside of the rotor liner 79. The third and sixth guiding elements 127, 130 define between them a groove in which a transfer tube 21 engaged in the second pinch valve member 43 and a transfer tube 20 engaged in the third pinch valve member 44 can be engaged so as to converge towards the inner surface of the rotor liner 79.

The bag cradle or loader 87 fits within the rotor liner 79, in which it can freely move along a direction parallel to the longitudinal axis of the rotor liner 79. The container 120, whose cross section is constant, forms a guiding member for the cradle 87 whose larger cross-section substantially corresponds to the inner cross-section of the rotor liner 79.

The cradle 87 has a longitudinal axis that coincides with the axis of rotation 31 of a rotor, when the bag cradle is fully engaged in the central compartment 34 of a rotor lined by the rotor liner 79.

The cradle 87 comprises a first, gutter-like, outer wall 88 having a height that substantially corresponds to the depth of the rotor liner 79; a U-shaped rim 140 is connected to the top of the first wall 88, which projects inwardly a lip 84 underneath which loops of transfer tubes can be stuck. As apparent in FIG. 15, the first wall 88 has an outer surface that is cylindrical, and an inner surface that is, save for a small upper cylindrical portion, frusto-conical. The inner frusto-conical surface has a central axis that coincides with the longitudinal axis of the cradle 87, which, in turn coincides with the axis of rotation 31 of a rotor, when the bag cradle is fully engaged in the central compartment 34 of a rotor lined by the rotor liner 79. The inner frusto-conical surface is therefore inclined with respect to the axis of rotation 31 of a rotor, when the bag cradle 87 is fully engaged in the central compartment 34 of a rotor.

The cradle further comprises a second, gutter-like wall 89 having a height that is about one fourth of the height of the first wall 88; the second wall 89 is connected to the lower part of the first wall 88, with their respective concavities facing each other, so as to form a closed wall. The dimensions of the two walls 88, 89 and the distance between them is so selected that the distance between any point of the inner wall 89 to the longitudinal axis of the cradle 87 is less than the distance from the longitudinal axis to the point (recesses 94, 95) of the outer wall 88 where the inlet/outlet of a satellite bag secured to the outer wall 88 is located.

The cradle further includes a flat bottom wall 90 connected to both first and second walls 88, 89 so as to form a receptacle 96 for containing a lower portion of satellite bags, and, as the case may be, a filter.

The cradle 87 also comprises means for securing the upper part of a stack of satellite bags inside and to the upper part of the first gutter-like wall 88. These securing means comprises two oblong holes 92 (locking means), in which the pegs 107, 108 of a bag holder 100 can be engaged. The length of the oblong holes 92 is a little less than the length of the rounded plates 109, 110 (complementary locking means) connected to the tip of the pegs 107, 108. The rounded plates 109, 110 are slightly flexible and can therefore be forced through the oblong holes 92, so as to anchor the bag holder 100 to the cradle 87. After completion of a separation process, the bag holder can be disengaged from the cradle 87 by simply pressing onto the oblong plates 109, 110 from outside of the cradle 87.

Between the locking means (oblong holes 92), the outer gutter-like wall 88 of the cradle 87 comprises, on its inner side, a U-shaped recess 94 for accommodating the end of one or two tubes embedded in the upper part of a satellite bag.

The cradle 87 also comprises a latching means by which it can be locked to the rotor liner 79 in a satellite bag loading/unloading position, in which the receptacle 96 forming the bottom part of the cradle 87 is below the flange 82, and the remaining part of the cradle 87 is above the flange 82.

The latching means comprises an elongated arm or latch 150, the upper end of which is hinged by a pivot 151 to the outer side of the outer wall 88 of the cradle 87, so as to extend in parallel to the median longitudinal axis of the wall 88. The latch is enclosed in a housing 152 that is so dimensioned as to allow the latch 150 to move between a first inward position, in which it is the closest to the outer wall 88, and a second outward position, in which it is the farthest from the outer wall 88. The latch 150 is spring-biased so as to return to the second position when not depressed. The housing 152 comprises a window 153 that exposes a corrugated outer portion 154 of the latch 150 that allows to press on the latch 150 and to move it from the second position into the first position. The latch 150 comprises a locking step 155 that protrudes outwards at its lower end.

The latching means also comprises an elongated flat U-shaped casing 156 connected to the wall 122 of larger curvature of the rotor liner 89, so dimensioned as to accommodate the latch 150 and its housing 152 and to keep the latch 150 slightly depressed. The casing 156 also helps guide the movement of the cradle 87 within the rotor liner 79 along a direction parallel to a central longitudinal axis of the rotor liner 79. The latching means also comprises a recess or catch 157 within the wall 122 of the cradle 87, at the level of the flange 82, which is slightly larger than the step 155 of the latch 150 so that the step 155 snaps into the catch 157 when the cradle 87 is lifted to the point that the locking step 155 faces the catch 157.

When the cradle 87 is locked in the upper part of the rotor liner 89, it is easy to access to the cradle 87 for securing thereto or removing therefrom a stack of satellite bags held together by a bag holder 100. If desired, this bag loading/unloading manipulation can also be performed outside of the separation apparatus, since the cradle 87 can be removed from the rotor liner 79 by simply depressing the latch 150 while lifting the cradle 87.

Variants of the rotor described above are as follows.

The cross-section of the gutter-like wall 88 of the cradle or bag loader 87, which, in the embodiments shown in the figures, has a semi circular cross-section, could have any concave shape adapted to partially surround a stack of satellite bags; for example it could be U-shaped or a sector of an ellipse. The portion of wall 88 that is tilted with respect to the rotation axis 31 of the rotor and forms a part of the support member for satellite bags can be integral with a wall of the central compartment 34. The rotor liner 79 can be an integral part of the rotor or it can be a removable liner fitting within the central compartment 34 of the rotor. The cradle 87, instead of being a removable part of the rotor liner 79, can be integral with the rest of the rotor liner 79. The internal surface of the cradle 87 (or, as a variant, of the central compartment 34) onto which a satellite bag full of liquid is pressed by centrifugal forces when the rotor is rotated can be substantially flat and tilted at an angle with respect to the rotation axis of the rotor allowing for a complete drainage of the satellite bag when the rotor is rotated. The cradle 87 (or the central compartment 34 if the latter is to include the tilted wall) can be fitted with two spaced apart pegs or hooks protruding inwards from an upper part thereof; these alternative pegs or hooks would be used to hang the satellite bags within the rotor instead of using the bag holder 100.

An example of a first separation protocol aiming at the preparation of three blood components, namely a plasma component essentially comprising plasma, a first blood cell component essentially comprising mononuclear cells and platelets, and a second blood cell component essentially comprising red blood cells, is explained below. This first separation protocol does not require the use of the channel sensor 58. The operation of the separation apparatus along the first separation protocol is as follows:

First stage (first protocol): a bag set as shown in FIG. 1, in which a satellite bag contains a volume of whole blood, is set in place in the rotor of a centrifuge (as shown in FIGS. 3, 4).

At the onset of the first stage, the first satellite bag 2 of the bag set of FIG. 1 contains a volume of anti-coagulated whole blood (usually about 500 ml). The collection tube 17 has been sealed and cut. The clamps 15 on the transfer tubes 14, 20, 21 connecting the satellite bags 2, 3, 4 to the separation bag 1 are closed. The frangible pin 16 blocking communication between the first satellite bag 2 and the separation bag 1 is broken as well as the frangible pin 23 blocking communication between the third satellite bag 4 and the separation bag 1. The first satellite bag 2 and the third satellite bags 4 are engaged on the first couple of pegs 107, 108 of a bag holder 100 (as shown in FIGS. 9, 10), the first satellite bag 2 being engaged first. The second satellite bag 3 is engaged on the second couple of pegs 111, 112. The bag holder 100 is mounted in a cradle 87 (as shown in FIGS. 6 to 8, and 12 to 15), as a result of which the first satellite bag 2 is adjacent to the inner surface of the cradle 87. The cradle 87 is inserted into the central compartment 34 of the centrifuge in which it is guided by the rotor liner 79. The satellite bags 2, 3, 4 are then substantially located on one side of a plane containing the rotation axis 31 of the rotor. The collection bag 1 is laid on the turntable 35 and the pins 83 on the flange 82 of the rotor liner 79 are engaged in the holes 12 of the disk-shaped connecting element 9 of the separation bag 1. The first transfer tube 14 connecting the first satellite bag 2 to the separation bag 1 is engaged in the first pinch valve member 42, the second transfer tube 20 connecting the second satellite bag 3 to the separation bag 1 is engaged in the third pinch valve member 44, and the third transfer tube 21 connecting the third satellite bag 4 to the separation bag 1 is engaged in the second pinch valve member 43. The clamps 15 on the transfer tubes 14, 20, 21 connecting the satellite bags 2, 3, 4 to the separation bag 1 are opened. The lid 49 of the rotor is closed.

Second stage (first protocol): the anti-coagulated whole blood contained in the first satellite bag 2 is transferred into the separation bag 1.

At the onset of the second stage, the first pinch valve member 42 is open and the second and third pinch valve members 43, 44 are closed. The rotor is set in motion by the centrifuge motor 40 and its rotation speed increases steadily until it reaches a first centrifugation speed (e.g. about 1500 RPM) that is so selected as To be high enough to cause the transfer, under centrifugation forces, of the content of the first satellite bag 2 into the separation bag 1;
To be high enough to cause the whole transfer to happen in the shorter period of time;
while, at the same time,
To be low enough not to cause pressure within the first satellite bag 2 to substantially exceed a determined pressure threshold above which hemolysis would occur;
To be low enough not to generate shearing forces in the flow of blood entering the separation bag 1 that would cause hemolysis.

It has been determined that the pressure threshold above which hemolysis occurs in the satellite bag 2 is about 10 PSI, and that the maximum rotation speed at which such pressure threshold is not reached and the shearing forces in the blood flow entering the separation bag do not cause hemolysis is about 1800 RPM. At a rotation speed of about 1500 RPM, it takes about one minute for transferring about 500 ml of anti-coagulated blood from the satellite bag 2 into the separation bag 1.

If the bag cell 56 has not detected red blood cell within a predetermined period of time following the start of the centrifugation process, the control unit 70 causes the rotor to stop and an alarm to be emitted. This could happen in particular if the frangible pin 16 has not been broken or if the clamp 15 on the first transfer tube 14 has not been opened.

Third stage (first protocol): the blood within the separation chamber is sedimented to a desired level.

At the onset of this stage, the pinch valve members 42, 43, 44 are closed. The rotor is rotated at a second, high centrifugation speed (for example, about 3200 RPM) for a predetermined period of time (for example, about 220 seconds) that is selected so that, whatever the hematocrit of the whole blood initially transferred in the separation bag 1, the blood sediments therein at the end of the predetermined period to a point where the hematocrit of the outer annular red blood cell layer is about 90 and the inner annular plasma layer is substantially devoid of cells. In more details, at the outcome of this sedimentation stage, the separation bag 1 exhibits four layers: a first inner layer mainly comprising plasma, a second intermediate layer mainly comprising platelets, a third intermediate layer mainly comprising mononuclear cells (lymphocytes and monocytes), and a fourth outer layer mainly comprising red blood cells (granulocytes remain embedded in the most inner layer of red blood cells).

Fourth stage (first protocol): a plasma component is transferred into the first satellite bag 2.

At the onset of this stage, the pinch valve members 42, 43, 44 are closed. The rotor is rotated at the same high centrifugation speed as in the sedimentation stage. After a predetermined period of time after the bag sensor 56 has stopped detecting red blood cells, which can happen before the end of the predetermined sedimentation period, the third pinch valve member 44 controlling the access to the second satellite bag 3 is opened and the pumping station 60 is actuated so as to pump hydraulic liquid at a constant flow rate (for example, about 220 ml/min) into the hydraulic chamber 55. The expanding hydraulic chamber 55 squeezes the separation bag 1 and causes the transfer of plasma into the second satellite bag 3. The pumping station 60 is stopped and the third pinch valve member 44 is closed after a predetermined period of time has elapsed following the detection of red blood cells by the bay sensor 57. A small volume of plasma (for example, about 5 ml) remains in the separation bag 1.

The transfer flow rate of the plasma component (which is directly related to the flow rate of the hydraulic fluid) is selected to be as high as possible without disturbing the platelet layer so as to avoid contaminating the plasma component with platelets.

Fifth stage (first protocol): a platelet/mononuclear cell component is transferred into the first satellite bag 2.

The fifth stage can start as soon as the third pinch valve member 44 is closed at the end of the fourth stage. At the onset of this fifth stage, the pinch valve members 42, 43, 44 are closed. The rotor is rotated at the same high centrifugation speed as previously. The first pinch valve member 42 controlling the access to the first satellite bag 2 is opened and the pumping station 60 is actuated so as to pump hydraulic liquid at a constant flow rate (for example, about 140 ml/min) into the hydraulic chamber 55. The expanding hydraulic chamber 55 squeezes the separation bag 1 and causes the transfer, into the first satellite bag 2, of a platelet/mononuclear cell component comprising the residual volume of plasma, the platelets, lymphocytes, monocytes and a small amount of red blood cells. The pumping station 60 is stopped and the first pinch valve member 42 is closed after a predetermined volume has been transferred into the first satellite bag 2, that is also after a predetermined amount of time has elapsed for a given hydraulic liquid flow rate. This predetermined volume of platelet/mononuclear cell component depends in part on the residual amount of plasma in the separation bag 1 at the end of the fourth stage. For example, when the residual volume of plasma in the separation bag 1 is determined by the bay sensor 57, the predetermined volume of the platelet/mononuclear cell component can be set at about between 10 and 15 ml, including about 5 ml of plasma and about 5 ml of red bloods cells.

Sixth stage (first protocol): the storage solution for red blood cells contained in the third satellite bag 3 is transferred into the separation bag 1.

The sixth stage can start as soon as the third pinch valve member 42 is closed at the end of the fifth stage. At the onset of this fifth stage, the pinch valve members 42, 43, 44 are closed. The rotor is rotated at the same high centrifugation speed as previously. The second pinch valve member 43 controlling the access to the third satellite bag 4 is opened, allowing the storage solution contained in the third satellite bag 3 to flow, under centrifugation forces, from the third satellite bag 3 into the separation bag 1, through the filter 22. After a predetermined period of time has elapsed after the opening of the second pinch valve member 43, the rotor is sharply braked so that its rotation speed decreases rapidly to a third, reduced speed (for example, 1500 RPM), so as to cause a suspension of the red blood cells contained in the separation bag in the storage solution and lower the viscosity thereof.

Seventh stage (first protocol): a red blood cell component is transferred into the third satellite bag 4.

The seventh stage can start after a predetermined period of time has elapsed after the rotor rotates at the third rotation speed. At the onset of this stage the second pinch valve member 43 controlling the access to the third satellite bag 4 is open and the pinch valve members 42, 44 are closed. The rotor rotates at the third rotation speed. The pumping station 60 is actuated so as to pump hydraulic liquid at a first flow rate into the hydraulic chamber 55 and consequently squeeze the separation bag 1 so as to cause the transfer, through the filter 22, of a red blood cell component into the third satellite bag 4. The first transfer flow rate of the red blood cell component (which is directly related to the flow rate of the hydraulic fluid) is selected to be as high as possible without damaging the red blood cells (hemolysis). When the pressure of the hydraulic liquid measured by the pressure gauge 67 reaches a first high pressure threshold, the flow rate of the hydraulic liquid is decreased from the first flow rate to a second flow rate. When the pressure of the hydraulic liquid measured by the pressure gauge 67 reaches a second high pressure threshold, the flow rate of the hydraulic liquid is further decreased from the second flow rate to a third flow rate. The second and third transfer flow rates of the red blood cell component are selected so that a maximal portion of the red blood cell component is transferred into the third satellite bag 4. The white blood cells (granulocytes and residual monocytes and lymphocytes) are trapped by the filter 22, so that the ultimate packed red blood cell component in the third satellite bag 4 is substantially devoid of white blood cells.

Eighth stage (first protocol): the centrifugation process is ended.

When a predetermined period of time (for example, about 30 seconds) has elapsed after the pressure of the hydraulic liquid has reached the second pressure threshold, the rotation speed of the rotor is decreased until the rotor stops, the pumping station 60 is actuated so as to pump the hydraulic liquid from the hydraulic chamber 55 at a high flow rate (for example, about 800 ml/min) until the hydraulic chamber 55 is empty, and the three pinch valve members 42, 43, 44 are actuated so as to seal and cut the tubes 14, 20, 21.

A variant of the first protocol is as follows. The bag set used does not comprise a third satellite bag and a leuko-reduction filter. When the plasma component has been transferred into the second satellite bag 3, all the blood cells (platelets, white cells and red blood cells), which remain in the separation bag 1, are transferred into the first satellite bag 2.

An example of a second separation protocol aiming at washing a volume of thawed glycerolized red blood cells, is explained below. This second separation protocol does not require the use of the second pinch valve member 43 nor does it require the channel sensor 58. The operation of the separation apparatus along the second separation protocol is as follows.

First stage (second protocol): a bag set as shown in FIG. 2, in which a satellite bag contains a volume of thawed glycerolized red blood cells, is set in place in the rotor of a centrifuge (as shown in FIGS. 3, 4).

At the onset of the first stage, a first satellite bag 2 containing a volume of thawed glycerolized red blood cells has been connected to the separation bag 1 by the first transfer tube 14. The second satellite bag 3, which contains a volume of wash liquid, and the first satellite bag 2 are engaged on the first couple of pegs 107, 108 of a bag holder 100 (as shown in FIGS. 9 and 10), the second satellite bag 3 being engaged first. The third satellite bag 4 is engaged on the second couple of pegs 111, 112. The bag holder 100 is mounted in a cradle 87 (as shown in FIGS. 6 to 8, and 12 to 15), as a result of which the first satellite bag 2 is adjacent to the inner surface of the cradle 87. The cradle 87 is inserted into the central compartment 34 of a centrifuge in which it is guided by the rotor liner 79. The satellite bags 2, 3, 4 are then substantially located on one side of a plane containing the rotation axis 31 of the rotor. The collection bag 1 is laid on the turntable 35 and the pins 83 on the flange 82 of the rotor liner 79 are engaged in the holes 12 of the disk-shaped connecting element 9 of the separation bag 1. The first transfer tube 14 connecting the first satellite bag 2 to the separation bag 1 is engaged in the first pinch valve member 42 and second transfer tube 20 connecting the second satellite bag 3 to the separation bag 1 is engaged in the third pinch valve member 44. The clamp 15 on the second transfer tube 20 is opened. The frangible pin 16 blocking communication between the first satellite bag 2 and the separation bag 1 is broken, as well as the frangible pin 25 blocking communication between the second satellite bag 3 and the separation bag 1, so that communication is established between the two satellite bags 2, 3 and the separation bag 1. The lid 49 of the rotor is closed.

Second stage (second protocol): the volume of thawed glycerolized red blood cells contained in the first satellite bag 2 is transferred into the separation bag 1.

This stage is substantially the same as the second stage of the first protocol. At the end of this stage the second satellite bag 3 containing the wash solution is stuck onto the inner surface of the cradle 87 by the centrifugal forces.

Third stage (second protocol): the thawed glycerolized red blood cells are sedimented to a desired level.

This stage is substantially the same as the third stage of the first protocol. At the outcome of this sedimentation stage, the separation bag 1 exhibits two layers: a first inner layer mainly comprising a supernatant (essentially glycerol) and a second outer layer comprising red blood cells.

Fourth stage (second protocol): the glycerol is transferred into the first satellite bag 2.

This stage is substantially the same as the fourth stage of the first protocol, except that the glycerol is transferred into the first satellite bag 2, which initially contained the volume of thawed glycerolized red blood cells.

Fifth stage (second protocol): a first volume of wash liquid is transferred from the second satellite bag 3 into the separation bag 1.

At the onset of this stage, the first and third pinch valve members 42, 44 are closed. The centrifuge rotates at the same high centrifugation speed as during the sedimentation stage. The third pinch valve member 44 is opened for a predetermined amount of time so as to allow the transfer, under centrifugation forces, of a first volume of wash liquid into the separation bag 1. For example, the third pinch valve member is opened for as long as it takes to transfer half of the volume of the wash liquid. Alternately, the third pinch valve member is opened until the bag sensor 56 detects a liquid in the separation bag 1.

Sixth stage (second protocol): the red blood cells are suspended in the first volume of wash liquid.

At the onset of this stage, the first and third pinch valve members 42, 44 are closed. The rotor is sharply braked so that its rotation speed decreases rapidly to a second, reduced speed so as to cause a suspension of the red blood cells contained in the separation bag in the wash liquid.

The next stages of the second protocol substantially repeat stages 3, 4, 5, 6, 3, 4: the red blood cells suspended in the first volume of wash liquid are separated by centrifugation, the supernatant (wash liquid and glycerol) is transferred into the first satellite bag 2 by the hydraulic station 60, a second volume of wash liquid (e.g. the second remaining half of the initial volume) is transferred under centrifugal forces into the separation bag 1, the red blood cells are suspended in the second volume of wash liquid and separated again by centrifugation, and the supernatant is transferred into the first satellite bag 2 by the hydraulic station 60. The washed red blood cells then remain in the separation bag 1.

Seventh stage (second protocol): the centrifugation process is ended.

The rotation speed of the rotor is decreased until the rotor stops, the pumping station 60 is actuated so as to pump the hydraulic liquid from the hydraulic chamber 55 at a high flow rate (for example, about 800 ml/min) until the hydraulic chamber 55 is empty, and the first and third pinch valve members 42, 44 are actuated so as to seal and cut the first and second transfer tubes 14 and 20. The washed red blood cells remain in the separation bag 1.

Eighth stage (second protocol): the washed blood cells are transferred into the third satellite bag 4.

The lid 49 of the rotor is opened and the separation bag 1 connected to the third satellite bag 4 is removed from the rotor. The clamp 15 on the third transfer tube 21 is opened. The frangible pin 23 blocking the communication between the third satellite bag 4 and the third transfer tube 21 connected thereto is broken. The storage solution contained in the third satellite bag 4 is allowed to flow by gravity into the separation bag, in which it mixes with the washed red blood cells. The content of the separation bag 1 is then allowed to flow by gravity into the third satellite bag 4. The third transfer tube 21 is sealed and cut.

It will be apparent to those skilled in the art that various modifications can be made to the apparatus and method described herein. Thus, it should be understood that the invention is not limited to the subject matter discussed in the specification. Rather, the present invention is intended to cover modifications and variation.

The invention claimed is:

1. An apparatus for separating a composite liquid into at least two components, comprising
   a rotor having a rotation axis, comprising
      a central compartment for containing at least one satellite bag connected to a separation bag;
      a removable bag loading means having a longitudinal axis, for loading and unloading the at least one satellite bag into and from the central compartment, comprising:
      an upper part comprising securing means for removably securing an upper portion of the at least one satellite bag to the removable bag loading means;
      a lower part comprising a receptacle for containing a lower portion of the at least one satellite bag; and
      an intermediate part connecting the upper part to the lower part and exposing an intermediate portion of the at least one satellite bag having an upper portion secured to the upper part of the loading means and a lower portion inserted in the receptacle; and
   a guiding means for guiding the removable bag loading means within the central compartment when inserting the removable bag loading means into and removing the removable bag loading means from the central compartment, and for positioning the removable bag loading means in a determined position within the rotor.

2. An apparatus according to claim 1, wherein the removable bag loading means further comprises a support means against which the at least one satellite bag is pressed under centrifugation forces during rotation of the rotor.

3. An apparatus according to claim 2, wherein the support means is so designed that the at least one satellite bag has a lower portion that is closer to the rotation axis than an upper portion, when the removable bag loading means is engaged in the central compartment and the upper portion of the at least one satellite bag is secured to the upper part of the removable bag loading means.

4. An apparatus according to claim 2, wherein the upper, intermediate, and lower part of the removable bag loading means comprise a continuous wall having an inner side facing the longitudinal axis of the removable bag loading means, wherein the support means includes a portion of the continuous wall.

5. An apparatus according to claim 4, wherein the portion of the inner side of the continuous wall has a surface that is tilted with respect to the rotation axis, when the removable bag loading means is engaged in the central compartment.

6. An apparatus according to claim 4, wherein a distance between the inner side of the portion of the continuous wall and the longitudinal axis of the removable bag loading means decreases from an upper part of the removable bag loading means to a lower part of the removable bag loading means, and the longitudinal axis of the removable bag loading means is substantially parallel to the rotation axis when the removable bag loading means is engaged in the central compartment.

7. An apparatus according to claim 4, wherein the portion of the inner side of the continuous wall is defined by a frustum of cone having an axis parallel to the longitudinal axis of the removable bag loading means, and the longitudinal axis of the removable bag loading means is substantially parallel to the rotation axis when the removable bag loading means is engaged in the central compartment.

8. An apparatus according to claim 4, wherein the lower part of the removable bag loading means comprises a curved wall connected to the continuous wall, wherein a distance between the curved wall and the longitudinal axis of the removable bag loading means decreases towards a lowest end of the removable bag loading means, and the support means includes a portion of the curved wall.

9. An apparatus according to claim 4, wherein the continuous wall has substantially a gutter-like shape.

10. An apparatus according to claim 1, wherein the guiding means positions the removable bag loading means in the central compartment so that the at least one satellite bag secured thereto is substantially located on one side of a plane containing the rotation axis.

11. An apparatus according to claim 1, wherein the longitudinal axis of the removable bag loading means substantially coincides with the rotation axis when the removable bag loading means is engaged in the central compartment, and the receptacle has an inner wall closest to the longitudinal axis that is so shaped that a distance between the inner wall to the longitudinal axis is less than a distance from the longitudinal axis to a point of the removable bag loading means where an upper inlet/outlet of the at least one satellite bag secured to the removable bag loading means is located.

12. An apparatus according to claim 1, wherein the securing means are designed to cooperate with a bag holder comprising:

an elongated body,
two peg-like members connected to the elongated body at a distance corresponding to a distance between two holes at the upper part of the at least one satellite bag, and
two retaining elements respectively connected at the ends of the peg-like members for preventing the at least one satellite bag engaged on the peg-like members of the bag holder from escaping therefrom.

13. An apparatus according to claim 12, wherein the upper part of the removable bag loading means comprises a wall and the securing means comprises two locking recesses in the wall in which the ends of the peg-like members of a bag holder can be engaged and removably locked therein by the retaining elements.

14. An apparatus according to claim 12, wherein the upper part of the removable bag loading means comprises a wall and the securing means comprises two apertures in the wall, in which the ends of the peg-like members of a bag holder can be engaged and removably locked therein by the retaining elements.

15. An apparatus according to claim 13, wherein the wall of the upper part of the removable bag loading means comprises two guides respectively extending from two lateral sides of the wall to the securing means, for guiding the peg-like members of a bag holder when the latter is pushed towards the wall for engaging the securing means.

16. An apparatus according to claim 1, wherein the upper part of the removable bag loading means comprises a wall having a recess for lodging the end of at least one tube embedded in the upper part of the at least one satellite bag.

17. An apparatus according to claim 1, wherein the upper part of the bag loading means comprises a wall having an upper edge with an inwardly projecting lip under which loops of tube can be stuck.

18. An apparatus according to claim 1, wherein the removable bag loading means further comprises a latching means for removably securing the removable bag loading means to the rotor in a position in which the removable bag loading means is partially engaged in the central compartment.

19. An apparatus according to claim 18, wherein the latching means secures the removable bag loading means to the rotor in a bag loading/unloading position in which at least the intermediate and upper part of the loading means protrude above an opening of the central compartment.

20. An apparatus according to claim 1, wherein the removable bag loading means has a regular cross section and the guiding means has a cross section which is at least partially complementary of the cross section of the removable bag loading means.

21. An apparatus according to claim 1, wherein the removable bag loading means comprises a cradle having a longitudinal axis that is substantially parallel to the rotation axis, wherein the cradle comprises a gutter-like wall having an inner concave surface facing the longitudinal axis, and wherein the concave surface is inclined with respect to the longitudinal axis so that the at least one satellite bag secured by a upper portion thereof within the upper part of the gutter-like wall, has a bottom portion that is closer to the longitudinal axis than an upper portion thereof.

22. An apparatus according to claim 21, wherein the inner concave surface of the gutter-like wall is generally frusto-conical.

23. An apparatus according to claim 21, wherein the cradle further comprises a containing wall connected to a lower part of the gutter-like wall so as to form a closed wall surrounding a lower portion of the at least one satellite bag secured to the gutter-like wall.

24. An apparatus according to claim 23, wherein a distance between the containing wall to the longitudinal axis is less than a distance from the longitudinal axis to a point of the gutter-like wall where an upper inlet/outlet of the at least one satellite bag secured to the removable bag loading means is located.

25. An apparatus according to claim 23, wherein the cradle further comprises a bottom wall connected to the gutter-like wall and the containing wall so as to form a receptacle for receiving a lower portion of the at least one satellite bag wherein the receptacle has a depth that is smaller than the length of the gutter-like wall.

26. An apparatus according to claim 25, wherein the bottom wall comprises a curved portion having a concavity oriented towards the rotation axis.

27. An apparatus according to claim 1, wherein the guiding means are designed to position the removable bag loading means within the central compartment so that the longitudinal axis of the removable bag loading means is substantially parallel to the rotation axis.

28. An apparatus according to claim 1, further comprising at least two pinch valve members for blocking or allowing a flow of fluid in a transfer tube connecting the at least one satellite bag to a separation bag, wherein each pinch valve member comprises a head including pinching jaws in which a portion of tube can be engaged, and the at least two pinch valve members are mounted on the rotor so that the heads thereof protrude at a periphery and above a level of an opening of the central compartment.

29. An apparatus according to claim 28, further comprising guiding elements for guiding a tube engaged in the pinching jaws of a pinch valve member into the central compartment along a determined direction.

30. An apparatus according to claim 28, further comprising guiding elements for guiding a tube engaged in the pinching jaws of a pinch valve member along a path substantially following an inner periphery of the central compartment.

31. An apparatus according to claim 1, wherein the guiding means comprises a container fitting within the central compartment of the rotor.

32. An apparatus according to claim 31, wherein the removable bag loading means has a cross section and the container comprises a wall having an inner cross section which is at least partially complementary of the cross section of the removable bag loading means.

33. An apparatus according to claim 31, wherein the container comprises an annular flange connected to an upper part thereof.

34. An apparatus according to claim 33, further comprising at least two pinch valve members for blocking or allowing a flow of fluid in a transfer tube connecting the at least one satellite bag to a separation bag, wherein each pinch valve member comprises a head including pinching jaws in which a portion of tube can be engaged, the at least two pinch valve members are mounted on the rotor so that the heads thereof protrude at a periphery and above a level of an opening of the central compartment, and the flange of the container comprises apertures though which the heads of the pinch valve members can extend.

35. An apparatus according to claim 34, wherein the guiding means further comprises guiding elements partially surrounding the apertures for the heads of the pinch valve members and defining gates for guiding a tube engaged in a pinch valve member into the container in a determined direction.

36. An apparatus according to claim 34, wherein the guiding means further comprises guiding elements for guiding a tube engaged in a pinch valve member along a path substantially following an inner periphery of the container.

37. A removable bag loader having a longitudinal axis, for loading and unloading the at least one satellite bag into and from the central compartment of a rotor having a rotation axis wherein the rotor is in an apparatus for separating a composite liquid into at least two components, the removable bag loader comprising:
- an upper part comprising a securing member for removably securing an upper portion of the at least one satellite bag to the removable bag loader;
- a lower part comprising a receptacle for containing a lower portion of the at least one satellite bag; and
- an intermediate part connecting the upper part to the lower part and exposing an intermediate portion of the at least one satellite bag having an upper portion secured to the upper part of the removable bag loader and a lower portion inserted in the receptacle.

38. A removable bag loader according to claim 37, wherein the removable bag loader further comprises a support member against which the at least one satellite bag is pressed under centrifugation forces during rotation of the rotor.

39. A removable bag loader according to claim 38, wherein the support member is such that the at least one satellite bag has a lower portion that is closer to the rotation axis than an upper portion, when the removable bag loader is engaged in the central compartment and the upper portion of the at least one satellite bag is secured to the upper part of the removable bag loader.

40. A removable bag loader according to claim 38, wherein the upper, intermediate, and lower part of the removable bag loader comprises a continuous wall having an inner side facing the longitudinal axis of the removable bag loader, wherein the support member includes a portion of the continuous wall.

41. A removable bag loader according to claim 40, wherein the portion of the inner side of the continuous wall has a surface that is tilted with respect to the rotation axis, when the removable bag loader is engaged in the central compartment.

42. A removable bag loader according to claim 40, wherein a distance between the inner side of the portion of the continuous wall and the longitudinal axis of the removable bag loader decreases from an upper part of the removable bag loader to a lower part of the removable bag loader, and the longitudinal axis of the removable bag loader is substantially parallel to the rotation axis when the removable bag loader is engaged in the central compartment.

43. A removable bag loader according to claim 40, wherein the portion of the inner side of the continuous wall is defined by a frustum of cone having an axis parallel to the longitudinal axis of the removable bag loader, and the longitudinal axis of the removable bag loader is substantially parallel to the rotation axis when the removable bag loader is engaged in the central compartment.

44. A removable bag loader according to claim 43, wherein the lower part of the removable bag loader comprises a curved wall connected to the continuous wall, wherein a distance between the curved wall and the longitudinal axis of the removable bag loader decreases towards a lowest end of the removable bag loader, and the support member includes a portion of the curved wall.

45. A removable bag loader according to claim 40, wherein the continuous wall has substantially a gutter-like shape.

46. A removable bag loader according to claim 37, wherein the longitudinal axis of the removable bag loader substantially coincides with the rotation axis when the removable bag loader is engaged in the central compartment, and the receptacle has an inner wall closest to the longitudinal axis that is so shaped that a distance between the inner wall to the longitudinal axis is less than a distance from the longitudinal axis to a point on the removable bag loader where an upper inlet/outlet of the at least one satellite bag secured to the removable bag loader is located.

47. A removable bag loader according to claim 37, wherein the securing member is designed to cooperate with a bag holder comprising:
- an elongated body,
- two peg-like members connected to the elongated body at a distance corresponding to a distance between two holes at the upper part of the at least one satellite bag, and
- two retaining elements respectively connected at the ends of the peg-like members for preventing the at least one satellite bag engaged on the peg-like members of a bag holder from escaping therefrom.

48. A removable bag loader according to claim 47, wherein the upper part of the removable bag loader comprises a wall and the securing member comprises two locking recesses in the wall in which the ends of the peg-like members of the bag holder can be engaged and removably locked therein by the retaining elements.

49. A removable bag loader according to claim 48, wherein the wall of the upper part of the removable bag loader comprises two guides respectively extending from two lateral sides of the wall to the securing member, for guiding the peg-like members of the bag holder when the latter is pushed towards the wall for engaging the securing member.

50. A removable bag loader according to claim 47, wherein the upper part of the removable bag loader comprises a wall and the securing member comprises two apertures in the wall, in which the ends of the peg-like members of the bag holder can be engaged and removably locked therein by the retaining elements.

51. A removable bag loader according to claim 37, wherein the upper part of the removable bag loader comprises a wall having a recess for accommodating the end of at least one tube embedded in the upper part of the at least one satellite bag.

52. A removable bag loader according to claim 37, wherein the upper part of the removable bag loader comprises a wall having an upper edge having an inwardly projecting a lip under which loops of tube can be stuck.

53. A removable bag loader according to claim 37, wherein the removable bag loader further comprises a latching member for removably securing the removable bag loader to the rotor in a position in which the removable bag loader is partially engaged in the central compartment.

54. A removable bag loader according to claim 53, wherein the latching member secures the removable bag loader to the rotor in a bag loading/unloading position in which at least the intermediate and upper part of the removable bag loader protrude above an opening of the central compartment.

55. A removable bag loader according to claim 37, wherein the removable bag loader comprises a cradle having a longitudinal axis that is substantially parallel to the rotation axis, wherein the cradle comprises a gutter-like wall having an inner concave surface facing the longitudinal axis, and wherein the concave surface is inclined with respect to the longitudinal axis so that the at least one satellite bag secured by a upper portion thereof, within the concave surface, to an upper part of the gutter-like wall, has a bottom portion that is closer to the longitudinal axis than an upper portion thereof.

56. A removable bag loader according to claim 55, wherein the inner concave surface of the gutter-like wall is generally frusto-conical.

57. A removable bag loader according to claim 55, wherein the cradle further comprises a containing wall connected to a lower part of the gutter-like wall so as to form a closed wall surrounding a lower portion of the at least one satellite bag secured to the gutter-like wall.

58. A removable bag loader according to claim 57, wherein a distance between the containing wall to the longitudinal axis is less than a distance from the longitudinal axis to a point on the gutter like wall where an upper inlet/outlet of the at least one satellite bag secured to the removable bag loader is located.

59. A removable bag loader according to claim 57, wherein the cradle further comprises a bottom wall connected to the gutter-like wall and the containing wall so as to form a receptacle for receiving a lower portion of the at least one satellite bag, wherein the receptacle has a depth that is smaller than the length of the gutter-like wall.

60. A removable bag loader according to claim 59, wherein the bottom wall comprises a curved portion having a concavity oriented towards the rotation axis.

* * * * *